US009133252B2

(12) United States Patent
Matoba et al.

(10) Patent No.: US 9,133,252 B2
(45) Date of Patent: Sep. 15, 2015

(54) POLYPEPTIDES HAVING ANTIVIRAL ACTIVITY AND METHODS FOR USE THEREOF

(71) Applicant: University of Louisville Research Foundation, Inc, Louisville, KY (US)

(72) Inventors: Nobuyuki Matoba, Owensboro, KY (US); Adam Husk, Louisville, KY (US); Sudha Sankaran, Newburgh, IN (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 14/325,040

(22) Filed: Jul. 7, 2014

(65) Prior Publication Data

US 2014/0314761 A1 Oct. 23, 2014

Related U.S. Application Data

(62) Division of application No. 13/808,444, filed as application No. PCT/US2011/043212 on Jul. 7, 2011, now Pat. No. 8,802,822.

(60) Provisional application No. 61/362,227, filed on Jul. 7, 2010, provisional application No. 61/368,343, filed on Jul. 28, 2010.

(51) Int. Cl.

| | |
|---|---|
| ***A61K 38/00*** | (2006.01) |
| ***A61K 38/16*** | (2006.01) |
| ***A61K 35/74*** | (2015.01) |
| ***A61K 39/395*** | (2006.01) |
| ***C12N 5/04*** | (2006.01) |
| ***C12N 15/00*** | (2006.01) |
| ***A61P 31/12*** | (2006.01) |
| ***A61P 31/18*** | (2006.01) |
| ***C07K 14/195*** | (2006.01) |
| ***C07K 14/36*** | (2006.01) |
| ***C07K 19/00*** | (2006.01) |
| ***C07K 14/37*** | (2006.01) |

(52) U.S. Cl.

CPC ............ *C07K 14/37* (2013.01); *C07K 2319/01* (2013.01); *C07K 2319/30* (2013.01)

(58) Field of Classification Search

None

See application file for complete search history.

(56) References Cited

U.S. PATENT DOCUMENTS

| | | | |
|---|---|---|---|
| 6,482,412 | B1 | 11/2002 | Tanaka et al. |
| 2008/0254507 | A1 | 10/2008 | Tanaka et al. |
| 2009/0297516 | A1 | 12/2009 | Mayo et al. |

OTHER PUBLICATIONS

Duvet et al. Hepatitis C Virus Glycoprotein Complex Localization in the Endoplasmic Reticulum Involves a Determinant for Retenetion and Not Retrieval. Jouranl of Biological Chemistry 1998, vol. 273, p. 32088-32095.*

Ritchie et al. Identification of N-linked carbohydrates from Severe Acute Respiratory Syndrome (SARS) Spike Glycoprotein. Virology 2010, vol. 399, p. 257-269.*

Mir-Shekari et al. The Glycosylation of the Influenza A Virus Hemagglutinin by Mammalian Cells. Journal of Biological Chemistry 1997, vol. 272, p. 4027-4036.*

Shi et al. Analysis of N-linked Glycosylation of Hantaan Virus Glycoproteins and the Role of Oligosaccharide Side Chains in Protein Folding and Intracellular Trafficking. Journal of Virology 2004, vol. 78 No. 10, p. 5414-5422.*

Brunetti et al. Herpes Simplex Virus L gD and Virions Accumulate in Endosomes by Mannose 6-Phosphate-Dependent and -Independent Mechanisms. Journal of Virology 1998, vol. 72 No. 4, p. 3330-3339.*

Liu et al. Intracellular Processing, Glycosylation, and Cell Surface Expression of Human Metapneumovirus Attachment Glycoprotein. Journal of Virology 2007, vol. 81 No. 24, p. 13435-13443.*

Rojek et al. Characterization of the cellular receptors for the South American hemorrhagic fever viruses Junin, Guanarito, and Machupo. Virology 2006, vol. 349, p. 476-491.*

Alouf JE, et al. (2003). "Staphylococcal and Streptococcal Superantigens: Molecular, Biological and Clinical Aspects." Int J Med Microbiol. 292:429-440.

Bachrach E, et al. (2005). "Effects of Virion Surface gp120 Density on Infection by HIV-1 and Viral Production by Infected Cells." Virology. 332:418-429.

Balzarini J, et al. (2006). "Mutational Pathways, Resistance Profile, and Side Effects of Cyanovirin Relative to Human Immunodeficiency Virus Type 1 Strains With N-glycan Deletions in Their gp120 Envelopes." J Virol. 80:8411-8421.

Botos I, et al. (2002). "Structures of the Complexes of a Potent Anti-HIV Protein Cyanovirin-N and High Mannose Oligosaccharides." J Biol Chem. 277:34336-34342.

Buonaguro L, et al. (2007). "Human Immunodeficiency Virus Type 1 Subtype Distribution in the Worldwide Epidemic: Pathogenetic and Therapeutic Implications." J Virol. 81:10209-10219.

(Continued)

*Primary Examiner* — Louise W Humphrey

(74) *Attorney, Agent, or Firm* — Stites & Harbison PLLC; Terry L. Wright

(57) ABSTRACT

A polypeptide is provided that comprises an actinohivin variant polypeptide having an amino acid sequence selected from SEQ ID NOS: 4-12. The polypeptide can be provided as part of a fusion protein that includes the actinohivin variant polypeptide and either a fragment crystallizable domain of an antibody (Fc), a fragment antigen-binding domain of an antibody (Fab), or a single chain variable fragment of an antibody (scFv). Isolated nucleic acid molecules encoding the polypeptides are also provided along with vectors and plant cells capable of expressing the polypeptides. Methods of treating an infection of a subject by an enveloped virus are further provided and include administering an effective amount of the polypeptides to a subject.

15 Claims, 8 Drawing Sheets

(56) References Cited

OTHER PUBLICATIONS

Buffa V, et al. (2009). “Cyanovirin-N Potently Inhibits Human Immunodeficiency Virus Type 1 Infection in Cellular and Cervical Explant Models.” J Gen Virol. 90:234-243.
Calarese DA, et al. (2005). “Dissection of the Carbohydrate Specificity of the Broadly Neutralizing Anti-HIV-1 Antibody 2G12.” Proc Natl Acad Sci U.S.A. 102:13372-13377.
Calarese DA, et al. (2003). “Antibody Domain Exchange is an Immunological Solution to Carbohydrate Cluster Recognition.” Science. 300:2065-2071.
Chiba H, et al. (2001). “A Simple Screening System for Anti-HIV Drugs: Syncytium Formation Assay Using T-Cell Line Tropic and Macrophage Tropic HIV env Expressing Cell Lines—Establishment and Validation.” J Antibiot (Tokyo). 54:818-826.
Chiba H, et al. (2001). “Actinohivin, a Novel Anti-HIV Protein From an Actinomycete That Inhibits Syncytium Formation: Isolation, Characterization, and Biological Activities.” Biochem Biophys Res Commun. 282:595-601.
Chiba H, et al. (2004). “Actinohivin, a Novel Anti-Human Immunodeficiency Virus Protein From an Actinomycete, Inhibits Viral Entry to Cells by Binding High-Mannose Type Sugar Chains of gp120.” Biochem Biophys Res Commun. 316:203-210.
Cutalo JM, et al. (2004). “Characterization of Glycopeptides From HIV-I(SF2) gp120 by Liquid Chromatography Mass Spectrometry.” J Am Soc Mass Spectrom. 15:1545-1555.
D’Souza MP, et al. (1995). “Neutralization of Primary HIV-1 Isolates by Anti-envelope Monoclonal Antibodies.” Aids. 9:867-874.
Elrefaei M, et al. (2004). “Central Memory CD4+ T Cell Responses in Chronic HIV Infection are not Restored by Antiretroviral Therapy.” J Immunol. 173:2184-2189.
Fenyo EM, et al. (2009). “International Network for Comparison of HIV Neutralization Assays: the NeutNet Report.” PLoS ONE. 4:e4505.
Forthal, et al. (2009). Curr Opin HIV AIDS, vol. 4, pp. 388-393.
Fraser JD, et al. (2008). “The Bacterial Superantigen and Superantigen-Like Proteins.” Immunol Rev. 225:226-243.
Garg AB, et al. (2009). “The Future of HIV Microbicides: Challenges and Opportunities.” Antivir Chem Chemother. 19:143-150.
Gavrovic-Jankulovic M, et al. (2008). “A Novel Recombinantly Produced Banana Lectin Isoform is a Valuable Tool for Glycoproteomics and a Potent Modulator of the Proliferation Response in CD3+, CD4+, and CD8+Populations of Human PBMCs.” Int J Biochem Cell Biol. 40:929-941.
Grant RM, et al. (2008). “Whither or wither microbicides?” Science, vol. 321, pp. 532-534.
Hansel, et al. (2010). “The Safety and Side Effects of Monoclonal Antibodies.” Nat Rev Drug Discov. 9:(4)325-38.
Hoorelbeke B, et al. (2010). “Actinohivin, a Broadly Neutralizing Prokaryotic Lectin, Inhibits HIV-1 Infection by Specifically Targeting High-Mannose-Type Glycans on the gp120 Envelope.” Antimicrobial Agents and Chemotherapy. 54(8):3237-3301.
Huskens D, et al. (2008). “Safety concerns for the potential use of cyanovirin-N as a microbicidal anti-HIV agent.” Int J Biochem Cell Biol. 40:2802-2814.
Inokoshi J, et al. (2001). “Molecular Cloning of Actinohivin, a Novel Anti-HIV Protein From an Actinomycete, and its Expression in *Escherichia Coli*.” Biochem Biophys Res Commun. 281:1261-1265.
Keller MJ, al. et al (2009). “Understanding Basic Mechanisms and Optimizing Assays to Evaluate the Efficacy of Vaginal Microbicides.” Sex Transm Dis. 36:592-95.
Lederman MM, et al. (2008). “Topical Application of Entry Inhibitors as “Virustats” to Prevent Sexual Transmission of HIV Infection.” Retrovirology. 5:116.
Leonard CK, et al. (1990). “Assignment of Intrachain Disulfide Bonds and Characterization of Potential Glycosylation Sites of the Type 1 Recombinant Human Immunodeficiency Virus Envelope Glycoprotein (gp120) Expressed in Chinese Hamster Ovary Cells.” J Biol Chem. 265:10373-10382.
Liedtke S, et al. (1997). “Host-Cell-Specific Glycosylation of HIV-2 Envelope Glycoprotein.” Glycoconj J. 14:785-793.
Lin G, et al. (2003). “Differential N-linked Glycosylation of Human Immunodeficiency Virus and Ebola Virus Envelope Glycoproteins Modulates Interactions With DC-SIGN and DC-SIGNR.” J Virol. 77:1337-1346.
Ma JK, et al. (2005). “Plant-Derived Pharmaceuticals—the Road Forward.” (2005). Trends Plant Sci. 10:580-585.
Marillonnet S, et al. (2005). “Systemic Agrobacterium Tumefaciens-Mediated Transfection of Viral Replicons for Efficient Transient Expression in Plants.” Nat Biotechnol. 23:718-723.
Marillonnet S, et al. (2004). “In planta engineering of viral RNA replicons: efficient assembly by recombination of DNA modules delivered by Agrobacterium.” Proc Natl Acad Sci U.S.A. 101:6852-6857.
Mascola JR, et al. (1996). “Human Immunodeficiency Virus Type 1 Neutralizing Antibody Serotyping Using Serum Pools and an Infectivity Reduction Assay.” AIDS Res Hum Retroviruses. 12:1319-1328.
Matoba N, et al. (2011) “Recombinant Protein Expression in Nicotiana.” Methods Mol Biol. 701:199-219.
Matoba N, et al. (2010). “HIV-1 Neutralization Profile and Plant-Based Recombinant Expression of Actinohivin, an Env Glycan-Specific Lectin Devoid of T-cell Mitogenic Activity.” PLoS One. 5(6):e11143.
Matoba N, et al. (2009). “Biochemical and Immunological Characterization of the Plant-Derived Candidate Human Immunodeficiency Virus Type 1 Mucosal Vaccine CTB-MPR(649-684).” Plant Biotechnol J. 7:129-145.
McGowan I. (2010). “Microbicides for HIV Prevention: Reality or Hope?” Curr Opin Infect Dis. 23:26-31.
Montefiori Dc. (2009). “Measuring HIV Neutralization in a Luciferase Reporter Gene Assay.” Methods Mol Biol. 485:395-405.
Moore, et al., (2010) “Engineered Fc variant antibodies with enhanced ability to recruit complement and mediate effector functions,” mAbs, vol. 2, pp. 181-189.
Morris GC, et al. (2010). “Microbicides and HIV Prevention: Lessons From the Past, Looking to the Future.” Curr Opin Infect Dis. 23:57-63.
O’Keefe BR, et al. (2009). “Scaleable Manufacture of HIV-1 Entry Inhibitor Griffithsin and Validation of its Safety and Efficacy as a Topical Microbicide Component.” Proc Natl Acad Sci U.S.A.
Paranjpe S, et al. (2002). “Subcompartmentalization of HIV-1 Quasispecies Between Seminal Cells and Seminal Plasma Indicates Their Origin in Distinct Genital Tissues.” AIDS Res Hum Retroviruses. 18:1271-1280.
Peters PJ, et al. (2006). “Non-Macrophage-Tropic Human Immunodeficiency Virus Type 1 R5 Envelopes Predominate in Blood, Lymph Nodes, and Semen: Implications for Transmission and Pathogenesis.” J Virol. 80:6324-6332.
Polonis VR, et al. (2008). “Recent Advances in the Characterization of HIV-1 Neutralization Assays for Standardized Evaluation of the Antibody Response to Infection and Vaccination.” Virology. 375:315-320.
Pope M, et al. (2003). “Transmission, Acute HIV-1 Infection and the Quest for Strategies to Prevent Infection.” Nat Med. 9:847-852.
Scanlan CN, et al. (2007). “Exploiting the Defensive Sugars of HIV-1 for Drug and Vaccine Design.” Nature. 446:1038-1045.
Scanlan CN, et al. (2002). “The Broadly Neutralizing Anti-Human Immunodeficiency Virus Type 1 Antibody 2G12 Recognizes a Cluster of Alpha1->2 Mannose Residues on the Outer Face of gp120.” J Virol. 76:7306-7321.
Sharon N, et al. (2004). “History of Lectins: From Hemagglutinins to Biological Recognition Molecules.” Glycobiology. 14:53R-62R.
Shenoy SR, et al. (2002). “Multisite and Multivalent Binding between Cyanovirin-N and Branched Oligomannosides: Calorimetric and NMR Characterization.” Chem Biol. 9:1109-1118.
Swanson MD, et al. (2010). “A Lectin Isolated From Bananas is a Potent Inhibitor of HIV Replication.” J Biol Chem 2010.
Takahashi A, et al. (2011). “The high Mannose-Type Glycan Binding Lectin Actinohivin: Dimerization Greatly Improves Anti-HIV Activity.” J Antibiot. (Tokyo), Epub ahead of print.

(56) References Cited

OTHER PUBLICATIONS

Takahashi A, et al. (2005). "Essential Regions for Antiviral Activities of Actinohivin, a Sugar-Binding Anti-Human Immunodeficiency Virus Protein From an Actinomycete." Arch Biochem Biophys. 437:233-240.
Taylor BS, et al. (2008). "The Challenge of HIV-1 Subtype Diversity." N Engl J Med. 358:1590-1602.
Tanaka H, et al. (2009). "Mechanism by Which the Lectin Actinohivin Blocks HIV Infection of Target Cells." Proc Nati Acad Sci U.S.A. 106:15633-15638.
Tsai CC, et al. (2004). "Cyanovirin-N Inhibits AIDS Virus Infections in Vaginal Transmission Models." AIDS Res Hum Retroviruses. 20:11-18.
Tsai CC, et al. (2003). "Cyanovirin-N Gel as a Topical Microbicide Prevents Rectal Transmission of SHIV89.6P in Macaques." AIDS Res Hum Retroviruses. 19:535-541.
Wang CY, et al. (1999). "Postexposure Immunoprophylaxis of Primary Isolates by an Antibody to HIV Receptor Complex." Proc Natl Acad Sci U.S.A. 96:10367-10372.
Willey RL, et al. (1996). "Differential Glycosylation, Virion Incorporation, and Sensitivity to Neutralizing Antibodies of Human Immunodeficiency Virus Type 1 Envelope Produced From Infected Primary T-Lymphocyte and Macrophage Cultures." J Virol. 70:6431-6436.
Yuste E, et. al. (2004). "Modulation of Env Content in Virions of Simian Immunodeficiency Virus: Correlation With Cell Surface Expression and Virion Infectivity." J Virol. 78:6775-6785.
Zhang M, et al. (2004). "Tracking Global Patterns of N-linked Glycosylation Site Variation in Highly Variable Viral Glycoproteins: HIV, SIV, and HCV Envelopes and Influenza Hemagglutinin." Glycobiology. 14:1229-1246.
Zeitlin L, et al. (2009). "Second-Generation HIV Microbicides: Continued Development of Griththsin." Proc Natl Acad Sci U.S.A. 106:6029-6030.
Zhu X, et al. (2000). "Mass Spectrometric Characterization of the Glycosylation Pattern of HIV-gp120 Expressed in CHO cells." Biochemistry. 39:11194-11204.
ISA/KR, International Preliminary report on Patentability and Written Opinion in corresponding International Application No. PCT/US11/43212 Mailed Jan. 17,2013.

* cited by examiner

ASVTIRNAQTGRLLDSNYNGNVYTLPANGGNYQRW
TGPGDGTVRNAQTGRCLDSNYDGAVYTLPCNGGSYQKW
LFYSNGYIQNVETGRVLDSNYNGNVYTLPANGGNYQKW
YTG

Actinohivin (AH)

FIG. 1A

AS*G*TIRNA*E*TGR*C*LDSNYNGNVYTLP*C*NGGNYQRW
TGPGDGTVRNA*E*TGRCLDSNYDGAVYTLPCNGGSYQKW
*TGPGD*G*T*IQN*A*ETGR*C*LDSNYNGNVYTLP*C*NGGNYQKW
TG

Actinohivin Variant 1 ($AH_{var1}$)

FIG. 1B

AS*G*TIRNA*E*TGR*C*LDSNY*D*G*A*VYTLP*C*NGG*S*YQRW
TGPGDGTVRNA*E*TGRCLDSNYDGAVYTLPCNGGSYQKW
*TGPGD*G*T*IQN*A*ETGR*C*LDSNY*D*G*A*VYTLP*C*NGG*S*YQKW
TG

Actinohivin Variant 2 ($AH_{var2}$)

FIG. 1C

AS*G*TIRNA*E*TGRLLDSNY*D*G*A*VYTLPANGG*S*YQRW
TGPGDGTVRNA*E*TGR*L*LDSNYDGAVYTLP*A*NGGSYQKW
*TGPGD*G*T*IQN*A*ETGR*L*LDSNY*D*G*A*VYTLPANGG*S*YQKW
TG

Actinohivin Variant 3 ($AH_{var3}$)

FIG. 1D

AS*G*TIRNAQTGRLLDSNYNGNVYTLPANGGNYQRW
TGPGDGTVRNAQTGR*L*LDSNY*N*G*N*VYTLP*A*NGG*N*YQKW
*TGPGD*G*T*IQN*AQ*TGRVLDSNYNGNVYTLPANGGNYQKW
TG

Actinohivin Variant 4 ($AH_{var4}$)

FIG. 1E

AS*G*TIRNA*E*TGRLLDSNYNGNVYTLPANGGNYQRW
TGPGDGTVRNA*E*TGR*L*LDSNY*N*G*N*VYTLP*A*NGG*N*YQKW
*TGPGD*G*T*IQN*A*ETGRVLDSNYNGNVYTLPANGGNYQKW
TG

Actinohivin Variant 5 ($AH_{var5}$)

FIG. 1F

ASVTIRNA*E*TGRLLDSNYNGNVYTLPANGGNYQRW
TGPGDGTVRNA*E*TGRCLDSNYDGAVYTLPCNGGSYQKW
LFYSNGYIQNVETGRVLDSNYNGNVYTLPANGGNYQKW
YTG

Actinohivin Variant 6 ($AH_{var6}$)

FIG. 1G

ASVTIRNA*E*TGR*C*LDSNYNGNVYTLP*C*NGGNYQRW
TGPGDGTVRNA*E*TGRCLDSNYDGAVYTLPCNGGSYQKW
LFYSNGYIQNVETGR*C*LDSNYNGNVYTLP*C*NGGNYQKW
YTG

Actinohivin Variant 7 ($AH_{var7}$)

FIG. 1H

AS*G*TIRNA*E*TGRLLDSNYNGNVYTLPANGGNYQRW
TGPGDGTVRNA*E*TGRCLDSNYDGAVYTLPCNGGSYQKW
*TGPGD*G*T*IQN*A*ETGRVLDSNYNGNVYTLPANGGNYQKW
TG

Actinohivin Variant 8 ($AH_{var8}$)

FIG. 1I

AS*G*TIRNAQTGR*C*LDSNYNGNVYTLP*C*NGGNYQRW
TGPGDGTVRNAQTGRCLDSNYDGAVYTLPCNGGSYQKW
*TGPGD*G*T*IQN*A*ETGR*C*LDSNYNGNVYTLP*C*NGGNYQKW
TG

Actinohivin Variant 9 ($AH_{var9}$)

FIG. 1J

POLYPEPTIDES HAVING ANTIVIRAL ACTIVITY AND METHODS FOR USE THEREOF

RELATED APPLICATIONS

This application is a divisional application of U.S. Application Ser.No. 13/808,444, which is a national stage entry of International Application No. PCT/US11/43212, which claims priority from U.S. Provisional Application Ser.No. 61/362,227, filed Jul. 7, 2010, and U.S. Provisional Application Ser.No. 61/368,343, filed Jul. 28, 2010, the entire disclosures of each of which are incorporated herein by this reference.

GOVERNMENT INTEREST

This invention was made with government support under grant number R21-AI 088585 provided by the National Institutes of Health and grant number W81XWH-09-2-0022 provided by the U.S. Army. The government has certain rights in this invention.

TECHNICAL FIELD

The presently-disclosed subject matter relates to polypeptides having antiviral activity. In particular, the presently-disclosed subject matter relates to polypeptides comprising an actinohivin (AH) polypeptide or an actinohivin variant ($AH_{var}$) polypeptide and having antiviral activity.

BACKGROUND

For a number of years, enveloped virus infections, including human immunodeficiency virus (HIV) infections, have posed serious global health concerns. Indeed, millions of new HIV infections are reported every year worldwide, with a majority of those new infections occurring mainly in developing regions where the availability of antiretroviral drug therapies is extremely limited, and, consequently, where Acquired Immunodeficiency Syndrome (AIDS) is among the leading causes of death [1]. The majority of infections are established via heterosexual transmission and condom use is currently the only available means to directly block this route of infection. As such, there is an urgent need for a woman-controlled, safe, effective, and inexpensive topical microbicide, at least until prophylaxis through vaccination becomes globally available [2, 3].

Current candidate microbicides include chemical and physical agents as well as biologicals, such as virion-inactivating agents, entry/fusion inhibitors, reverse transcriptase inhibitors, and a number of others. At this point in time, however, it is not known which type of anti-HIV agents will prove to be the most effective topical microbicides and, indeed, the blocking of HIV-1 mucosal transmission may require combinations of multiple agents [4, 5]. Therefore, to broaden the options for different combinations in HIV-1 microbicide development, it has been recognized that it is important to expand the candidate portfolio in each category of possible microbicide components.

In this regard, it has recently been further recognized that envelope (Env) glycans may constitute an attractive target for entry/fusion inhibitor-based microbicide development as Env glycans play critical roles in broad aspects of the viral life cycle ranging from Env folding in host cells to viral transmission and immune escape [7]. Indeed, it has been observed that the envelope (Env) gp120 is heavily glycosylated with N-linked glycans (NLGs), and generally accounts for more than half of the protein's molecular mass [6], with high-mannose-type glycans (HMGs) representing the major class.

Along these lines, lectins have attracted considerable attention in the search for Env glycan-targeting microbicide candidates as various naturally-occurring lectins have been shown to possess anti-HIV activities. Examples include algae-derived cyanovirin-N(CV-N) and griffithsin (GRFT), as well as plant-derived concanavalin A (Con A) and snowdrop lectin, among others [7]. More recently, a Jacalin-related lectin isolated from the banana fruit was shown to potently inhibit HIV-1 entry into target cells [8]. Although conceptually not a lectin, the human monoclonal antibody (mAb) 2G12 has also been shown to specifically bind to gp120 HMGs and thereby neutralize a wide spectrum of HIV-1 strains; thus, it has also been counted among the very few broadly neutralizing mAbs isolated to date [9,10].

One particular lectin that has recently been noted as having anti-HIV activity is actinohivin (AH). AH was first isolated from the actinomycete strain *Longispora albida* K97-0003$^T$ based on the inhibitory activity that was displayed in a syncytium formation assay [11]. Recent crystallographic analysis has revealed that AH is a monomeric protein and possesses three carbohydrate-binding (i.e., sugar-binding) domains [12]. Unlike several other known monosaccharide-specific anti-HIV lectins such as GRFT, Con A, and *Galanthus nivalis* agglutinin [7], however, AH specifically recognizes a cluster of multiple HMGs via a collaborative action among the protein's three sugar-binding sites [12, 13]. Because clustering HMGs is a unique feature of Env glycans and is not usually found on host human proteins [14], AH has been hypothesized to be a better anti-HIV-1 lectin with greater specificity to the virus. To date, however, and despite the detailed studies of AH's carbohydrate-binding specificity [12, 13, 15], limited investigation has been undertaken with respect to the protein's potential anti-HIV activity and with respect to how the protein may be manipulated to produce commercially relevant amounts and/or to provide increased anti-HIV activity.

SUMMARY

The presently-disclosed subject matter meets some or all of the above-identified needs, as will become evident to those of ordinary skill in the art after a study of information provided in this document. This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature (s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter relates to polypeptides comprising an actinohivin (AH) polypeptide or an actinohivin variant ($AH_{var}$) polypeptide, and having antiviral activity. In some embodiments of the presently-disclosed subject matter, a polypeptide is provided that comprises an $AH_{var}$ polypeptide having an amino acid sequence selected from SEQ ID NOS: 4-12. In some embodiments, the $AH_{var}$ polypeptide comprises the sequence of SEQ ID NO: 4. In some embodiments, the $AH_{var}$ polypeptide further comprises and endomembrane system (EMS)-targeting signal peptide, such as that provided in SEQ ID NO: 15.

In some embodiments of the presently-disclosed polypeptides, a polypeptide is provided in which the $AH_{var}$ polypeptide is provided as part of a fusion protein. For example, in some embodiments, an $AH_{var}$ polypeptide is provided along with a second polypeptide selected from: a fragment crystallizable domain of an antibody (Fc); a fragment antigen-binding domain of an antibody (Fab); or a single chain variable fragment of an antibody (scFv), such that the $AH_{var}$ polypeptide and the second polypeptide form a fusion protein. In some embodiments, the $AH_{var}$ polypeptide and the second polypeptide are connected via a peptide linker, such as that provided in SEQ ID NO: 3. In certain of these embodiments, the antibody domains used in these fusion proteins are derived from a monoclonal antibody.

In further embodiments of the presently-disclosed subject matter, fusion proteins are provided that comprise a native actinohivin polypeptide. For example, in some embodiments, a fusion polypeptide is provided that comprises an actinohivin polypeptide; and a second polypeptide selected from: a fragment antigen-binding domain of an antibody (Fab); and a single chain variable fragment of an antibody (scFv).

Further provided, in some embodiments of the presently-disclosed subject matter, are isolated nucleic acid molecules. In some embodiments, an isolated nucleic acid molecule is provided that comprises a sequence that encodes an actinohivin variant polypeptide having an amino acid sequence selected from SEQ ID NOS: 4-12. In some embodiments, the nucleic acid molecule comprises the amino acid sequence of SEQ ID NO: 4. In some embodiments, the nucleic acid molecule comprises the nucleic acid sequence of SEQ ID NO: 3.

In some embodiments, the isolated nucleic acid molecules of the presently-disclosed subject matter are provided as part of a vector that, in certain embodiments, includes an expression control sequence operably linked to the isolated nucleic acid molecules. In some embodiments, a plant cell is provided that has been transfected with such a vector to thereby provide a plant cell, or a progeny thereof, that expresses the actinohivin variant polypeptide. In some embodiments, the plant cell is a *Nicotiana benthamiana* plant cell.

Still further provided, in some embodiments of the present disclosed subject matter, are pharmaceutical compositions. In some embodiments, a pharmaceutical composition is provided that comprises an $AH_{var}$ polypeptide having an amino acid sequence selected from SEQ ID NOS: 4-12 and a pharmaceutically-acceptable vehicle, carrier, or excipient.

In yet further embodiments of the presently-disclosed subject matter, therapeutic and/or prophylactic methods are provided that make use of the polypeptides described herein. In some embodiments, a method of treating an infection of a subject by an enveloped virus is provided. In some embodiments, a method of treating an infection of a subject by an enveloped virus is provided that includes the step of administering to the subject an effective amount of an $AH_{var}$ polypeptide having an amino acid sequence selected from SEQ ID NOS: 4-12. In some embodiments, the enveloped virus is a human immunodeficiency virus (HIV), an influenza virus, a hanta virus, a hepatitis C virus, a herpes virus, a severe acute respiratory syndrome coronavirus (SARS-CoV), a metapneumovirus, a henipavirus, a flavivirus, or a hemorrhagic fever virus. In some embodiments, administering the $AH_{var}$ polypeptide to the subject comprises topically administering the $AH_{var}$ polypeptide.

Further features and advantages of the presently-disclosed subject matter will become evident to those of ordinary skill in the art after a study of the description, figures, and non-limiting examples in this document.

BRIEF DESCRIPTION OF THE DRAWINGS

FIGS. 1A-1J includes amino acid sequences of a native actinohivin (AH) polypeptide (FIG. 1A, SEQ ID NO: 2) and of nine actinohivin variant ($AH_{var1-9}$) polypeptides (FIGS. 1B-1J; SEQ ID NOS: 4-12, respectively) of the presently-disclosed subject matter, where the carbohydrate-binding domains of the polypeptides are underlined, wherein non-underlined residues comprise hinge or terminal extension regions of the polypeptides, and where the amino acid residues that are changed relative to the native AH amino acid sequence are shown in bold and italic font;

BRIEF DESCRIPTION OF THE SEQUENCE LISTING

Figure 2:
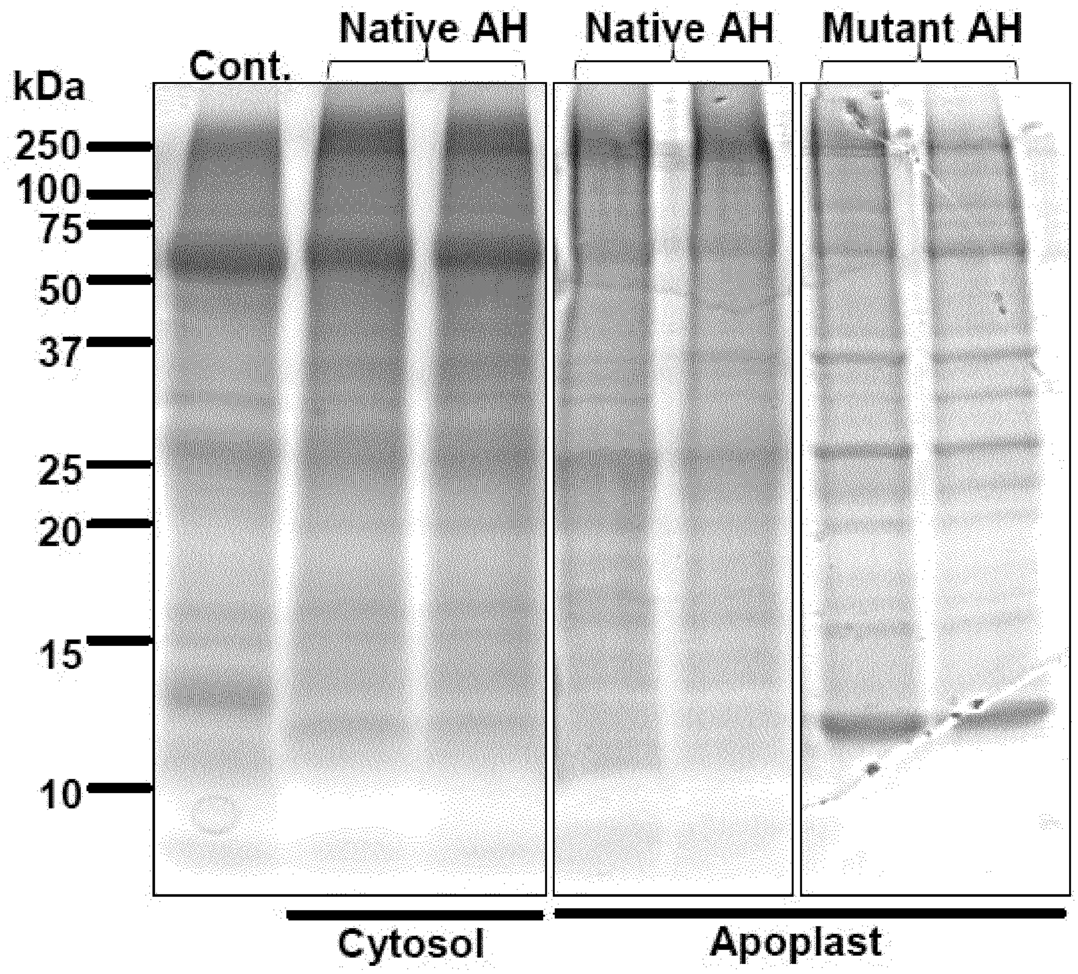
FIG. 2 is an image of a gel showing the SDS-PAGE analysis of the amounts of native AH polypeptides (Native AH) and $AH_{var1}$ polypeptides (Mutant AH) produced in *Nicotiana benthamiana* plants.

SEQ ID NO: 1 is a nucleic acid sequence encoding a native actinohivin (AH) polypeptide;

SEQ ID NO: 2 is an amino acid sequence of a native AH polypeptide;

SEQ ID NO: 3 is a nucleic acid sequence encoding a first exemplary actinohivin variant ($AH_{var1}$) polypeptide made in accordance with the presently-disclosed subject matter;

SEQ ID NO: 4 is an amino acid sequence of the $AH_{var1}$ polypeptide;

SEQ ID NO: 5 is an amino acid sequence of a second exemplary actinohivin variant ($AH_{var2}$) polypeptide made in accordance with the presently-disclosed subject matter;

SEQ ID NO: 6 is an amino acid sequence of a third exemplary actinohivin variant ($AH_{var3}$) polypeptide made in accordance with the presently-disclosed subject matter;

SEQ ID NO: 7 is an amino acid sequence of a fourth exemplary actinohivin variant ($AH_{var4}$) polypeptide made in accordance with the presently-disclosed subject matter;

SEQ ID NO: 8 is an amino acid sequence of a fifth exemplary actinohivin variant ($AH_{var5}$) polypeptide made in accordance with the presently-disclosed subject matter;

SEQ ID NO: 9 is an amino acid sequence of a sixth exemplary actinohivin variant ($AH_{var6}$) polypeptide made in accordance with the presently-disclosed subject matter;

SEQ ID NO: 10 is an amino acid sequence of a seventh exemplary actinohivin variant ($AH_{var7}$) polypeptide made in accordance with the presently-disclosed subject matter;

SEQ ID NO: 11 is an amino acid sequence of an eighth exemplary actinohivin variant ($AH_{var8}$) polypeptide made in accordance with the presently-disclosed subject matter; and SEQ ID NO: 12 is an amino acid sequence of a ninth exemplary actinohivin variant ($AH_{var9}$) polypeptide made in accordance with the presently-disclosed subject matter;

SEQ ID NO: 13 is an amino acid sequence of a peptide linker;

SEQ ID NO: 14 is a nucleic acid sequence encoding an endomembrane system (EMS)-targeting signal peptide; and SEQ ID NO: 15 is an amino acid sequence of an endomembrane system (EMS)-targeting signal peptide.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

As will be recognized by those skilled in the art, certain polypeptides and nucleotides described herein can be found in publicly-accessible databases, such as in the GENBANK® and SWISSPROT databases. The sequences contained in such databases are incorporated herein by reference as are equivalent and related sequences present in GENBANK®, SWISSPROT, or other public databases. Also expressly incorporated herein by reference are all annotations present in the GENBANK® and SWISSPROT databases associated with the polypeptides and nucleotides described herein. Unless otherwise indicated or apparent, the references to the GENBANK® database and the SWISSPROT database are references to the most recent version of the database as of the filing date of this Application.

While the following terms used herein are believed to be well understood by one of ordinary skill in the art, definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms “a”, “an”, and “the” refer to “one or more” when used in this application, including the claims. Thus, for example, reference to “a cell” includes a plurality of such cells, and so forth.

Unless otherwise indicated, all numbers expressing quantities of ingredients, properties such as reaction conditions, and so forth used in the specification and claims are to be understood as being modified in all instances by the term “about.” Accordingly, unless indicated to the contrary, the numerical parameters set forth in this specification and claims are approximations that can vary depending upon the desired properties sought to be obtained by the presently-disclosed subject matter.

As used herein, the term “about,” when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods.

Actinohivin (AH) is an actinomycete-derived lectin that is produced as a monomeric protein having three carbohydrate-binding sites or domains [12]. AH has been found to specifically bind to high-mannose-type glycans (HMGs) found on the envelope (Env) of a number of enveloped viruses and, more specifically, has been found to specifically bind to a cluster of HMGs uniquely found on the HIV-1 Env such that AH is capable of eliciting nanomolar antiviral activity against multiple HIV strains. Analyses have revealed that AH has a high safety profile in human peripheral blood mononuclear cells (PBMCs) and in a rabbit vaginal irritation assay, and it has been further demonstrated that a translational AH-AH fusion protein exhibits stronger and broader anti-HIV-1 activity than the original monomeric protein, potentially due to stronger binding to the target as a result of high avidity and/or better cross-linking of Env [61]. It has now been discovered that modifications can be made in the AH amino acid sequence to provide actinohivin variant ($AH_{var}$) polypeptides that can be provided alone (e.g., as monomers or dimers) or in the form of a fusion proteins, and that have surprisingly superior properties relative to a native AH polypeptide. For example, in some embodiments, polypeptides comprising an $AH_{var}$ have reduced hydrophobicity and surface charge properties (e.g., isoelectric point [pI]) as compared to native AH polypeptide, which allows for the $AH_{var}$ polypeptides to be expressed at higher levels in plant cells and also allows the $AH_{var}$ polypeptides to be more readily extracted and purified. For another example, in some embodiments, polypeptides comprising $AH_{var}$ have improved stability as compared to native AH polypeptides.

In some embodiments, the presently-disclosed subject matter thus provides isolated polypeptides that comprise an $AH_{var}$ polypeptide. In some embodiments, an $AH_{var}$ polypeptide is provided that has an amino acid sequence selected from SEQ ID NOS: 4-12. In some embodiments, the $AH_{var}$ polypeptide comprises the amino acid sequence of SEQ ID NO: 4.

The term “isolated,” when used in the context of an isolated polypeptide, or an isolated nucleic acid, is a polypeptide, or nucleic acid, that, by the hand of man, exists apart from its native environment and is therefore not a product of nature. An isolated polypeptide or nucleic acid can exist in a purified form or can exist in a non-native environment such as, for example, in a transgenic host cell.

The term “native”, when used with reference to a polypeptide, refers to a polypeptide that is encoded by a gene that is naturally present in the genome of an untransformed cell. In this regard, the term “gene” is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, native proteins, homologs, orthologs, paralogs, fragments and other equivalents, variants, and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. A fragment can also be a "functional fragment," in which case the fragment retains some or all of the activity of the reference polypeptide as described herein. For example, a functional fragment of an AH polypeptide can retain some or all of the ability of the reference polypeptide to bind carbohydrates, such as HMGs.

The terms "modified amino acid", "modified polypeptide", and "variant" refer to an amino acid sequence that is different from the reference polypeptide by one or more amino acids, e.g., one or more amino acid substitutions. A variant of a reference polypeptide also refers to a variant of a fragment of the reference polypeptide, for example, a fragment wherein one or more amino acid substitutions have been made relative to the reference polypeptide. A variant can also be a "functional variant," in which the variant retains some or all of the activity of the reference protein as described herein. For example, in some embodiments, an $AH_{var}$ polypeptide can retain some or all of the ability of a native AH polypeptide to bind HMGs.

The term functional variant also includes a functional variant of a functional fragment of a reference polypeptide. The term functional variant further includes conservatively substituted variants. The term "conservatively substituted variant" refers to a peptide comprising an amino acid residue sequence that differs from a reference peptide by one or more conservative amino acid substitutions, and maintains some or all of the activity of the reference peptide as described herein. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. The phrase "conservatively substituted variant" also includes peptides wherein a residue is replaced with a chemically-derivatized residue, provided that the resulting peptide maintains some or all of the activity of the reference peptide as described herein.

As noted, in some embodiments, the polypeptides of the presently-disclosed subject matter include more than one AH or $AH_{var}$ polypeptide. For example, in some embodiments, the polypeptide can include two $AH_{var}$ polypeptides such that the $AH_{var}$ polypeptides are provided as a dimer. As another example, in some embodiments, the polypeptides can include an $AH_{var}$ polypeptide and an AH polypeptide.

In some embodiments of the presently-disclosed polypeptides, the AH and/or $AH_{var}$ polypeptides can be provided as part of a fusion protein such that a protein can be provided that confers antibody-dependent cell-mediated cytotoxicity, complement-dependent cytotoxicity, antibody-dependent cellular phagocytosis, antibody-dependent cell-mediated virus inhibition, and/or a longer serum half life. In some embodiments, a fusion protein is provided that includes: an $AH_{var}$ polypeptide having an amino acid sequence selected from SEQ ID NOS: 4-12; and a second polypeptide selected from a fragment crystallizable domain of an antibody (Fc); a fragment antigen-binding domain of an antibody (Fab); and a single chain variable fragment of an antibody (scFv), wherein the $AH_{var}$ polypeptide and the second polypeptide together comprise the fusion protein. For example, in some embodiments, the fusion protein includes an $AH_{var}$ polypeptide and the fragment crystallizble (Fc) domain of a human monoclonal immunoglobulin (Ig) G ($AH_{var}$-Fc). As another example, in some embodiments, a fusion protein can be provided that includes an $AH_{var}$ polypeptide and the fragment antigen binding (Fab) domain of a human monoclonal antibody. As yet another example, in some embodiments, a fusion protein can be provided that includes an $AH_{var}$ polypeptide and the single chain variable fragment (scFv) domain of an antibody.

In some embodiments of the fusion proteins described herein, a fusion protein is provided that includes a native AH polypeptide and a second polypeptide selected from a Fab fragment and a scFv fragment.

As used herein, the phrase "fusion polypeptide" or "fusion protein" is used to refer to a polypeptide made up of two or more amino acid sequences representing peptides or polypeptides from different sources. In some embodiments, a peptide linker sequence may be employed to separate the first and the second polypeptides by a distance sufficient to ensure that each polypeptide folds into its secondary and tertiary structures. Such a peptide linker sequence can be incorporated into the fusion protein using standard techniques well known in the art, and can be chosen based on: (1) the ability of the linker sequence to adopt a flexible extended conformation; (2) the ability of the linker sequence to adopt a secondary structure that could interact with functional domains on the first and second polypeptides; and (3) the lack of hydrophobic or charged residues that might react with the polypeptide functional domains. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8562, 1986; U.S. Pat. No. 4,935,233 and U.S. Pat. No. 4,751,180. In some embodiments, the linker sequence can be from 1 to about 50 amino acids in length. In some embodiments, the linker comprises an amino acid sequence of SEQ ID NO: 13.

Fusion proteins in accordance with the presently-disclosed subject matter can be produced by a variety of methods known to those of ordinary skill in the art. For example, in some embodiments, a fusion protein comprising an $AH_{var}$ polypeptide and the Fc region of human immunoglobulin (Ig)G can be produced by attaching the nucleic acid sequence encoding the hinge and the Fc region of human IgG to the 3' end of an $AH_{var}$ polypeptide coding sequence, such as that provided in SEQ ID NO: 3, via the use of a coding sequence for a flexible peptide linker (e.g., Gly-Gly-Gly-Ser; SEQ ID NO: 13). In some embodiments, the constructed nucleic acid sequence is then inserted into an appropriate vector for expression of the fusion protein in a desired cell. In some embodiments, such as those where the fusion polypeptides are to be produced in plants, a nucleic acid coding sequence for an endomembrane system (EMS)-targeting signal peptide, such as what is provided in SEQ ID NOS: 14 and 15 as well as those derived from tobacco calreticulin, *N. benthamiana* chitinases, and others can further be attached to the 5' end of the nucleic acid sequence encoding the $AH_{var}$ polypeptide. Of course, various other methods and signal sequences can also be used in accordance with the production of the presently-disclosed $AH_{var}$ polypeptides as would be understood by those of ordinary skill in the art.

As noted, in some embodiments of the fusion proteins described herein, the antibody fragments used in accordance with the presently-disclosed subject matter are monoclonal antibody fragments. However, any antibody or fragments thereof which effectively confer antibody-dependent cellular cytotoxicity, complement-dependent cytotoxicity, and/or longer serum half life to the AH or $AH_{var}$ polypeptides described herein are within the scope of the presently-disclosed subject matter. This includes by way of example, monoclonal antibodies, recombinant antibodies, chimeric antibodies, humanized antibodies, bispecific antibodies, catalytic antibodies, single chain antibodies, antibodies from different species (e.g., mouse, goat, rabbit, human, rat, bovine, llama, etc.), anti-idiotypic antibodies, antibodies of different isotype (IgG, IgM, IgE, IgA, etc.), as well as fragments and derivatives thereof (e.g., $(Fab)_2$, Fab, Fv, Fab, 2(Fab), Fab', $(Fab)_2$ fragments).

Further provided, in some embodiments of the presently-disclosed subject matter, are isolated nucleic acids encoding one or more of the polypeptides described herein (i.e., an $AH_{var}$ polypeptide). In some embodiments, an isolated nucleic acid molecule is provided that comprising a sequence encoding an $AH_{var}$ polypeptide having an amino acid sequence selected from SEQ ID NOS: 4-12. In some embodiments, an isolated nucleic acid molecule is provided that comprises the sequence of SEQ ID NO: 3.

The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "degenerate variant" refers to a nucleic acid having a residue sequence that differs from a reference nucleic acid by one or more degenerate codon substitutions. Degenerate codon substitutions can be achieved by generating sequences in which the third position of one or more selected (or all) codons is substituted with mixed base and/or deoxyinosine residues (Batzer, et al. 1991; Ohtsuka, et al. 1985; Rossolini, et al. 1994).

In some embodiments, an isolated nucleic acid sequence is provided that selectively hybridizes to the sequence of SEQ ID NO: 3. The term "selectively hybridize" as used herein refers to the ability of a nucleic acid sequence to hybridize to a target polynucleotide (e.g., a polynucleotide of SEQ ID NO: 3) with specificity. Thus, the nucleic acid sequence comprises a polynucleotide sequence that is complementary, or essentially complementary, to at least a portion of the target polynucleotide sequence. For example, in some embodiments, the nucleic acid sequence that selectively hybridizes to the sequence of SEQ ID NO: 3 is complementary to the sequence of SEQ ID NO: 3. Nucleic acid sequences which are "complementary" are those which are base-pairing according to the standard Watson-Crick complementarity rules. As used herein, the term "complementary sequences" means nucleic acid sequences which are substantially complementary, as can be assessed by the same nucleotide comparison set forth above, or as defined as being capable of hybridizing to the nucleic acid segment in question under relatively stringent conditions such as those described herein. A particular example of a contemplated complementary nucleic acid segment is an antisense oligonucleotide. With regard to the nucleic acid sequences disclosed herein as selectively hybridizing to the sequence of SEQ ID NO: 3, the hybridizing nucleic acid sequence need not necessarily be completely complementary to the nucleic acid of SEQ ID NO: 3 along the entire length of the target polynucleotide so long as the hybridizing nucleic acid sequence can bind the nucleic acid of SEQ ID NO: 3 with specificity. In some embodiments, the nucleic acid sequences that selectively hybridize to the sequence of SEQ ID NO: 3 are about 80%, about 85%, about 90%, about 95%, about 98%, or about 100% complementary to the sequence of SEQ ID NO: 3.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. For example, in some embodiments, nucleic acid hybridization can be performed at 60° C. with 0.1× sodium citrate-sodium chloride (SSC) and 0.1% sodium dodecyl sulfate (SDS). However, the combination of parameters is much more important than the measure of any single parameter. (See, e.g., Wetmur & Davidson, 1968). Determining appropriate hybridization conditions to identify and/or isolate sequences containing high levels of homology is well known in the art. (See, e.g., Sambrook, et al., 1989).

In some embodiments of the presently-disclosed subject matter, vectors that include one or more of the isolated nucleic acid sequences disclosed herein are provided. In some embodiments, a vector is provided that includes an isolated nucleic acid comprising a sequence of SEQ ID NO: 3. In some embodiments, a vector is provided that includes an isolated nucleic acid sequence that encodes an $AH_{var}$ polypeptide having an amino acid sequence selected from SEQ ID NOS: 4-12. In some embodiments, a vector is provided that includes an isolated nucleic acid sequence that encodes a polypeptide comprising an amino acid sequence of SEQ ID NO: 4.

The term "vector" is used herein to refer to any vehicle that is capable of transferring a nucleic acid sequence into a cell. For example, vectors which may be used in accordance with the presently-disclosed subject matter include, but are not limited to, plasmids, cosmids, bacteriophages, or viruses, which can be transformed by the introduction of a nucleic acid sequence of the presently-disclosed subject matter. Such vectors are well known to those of ordinary skill in the art. In some embodiments, the vectors of the presently-disclosed subject matter are plasmids. In other embodiment of the presently-disclosed subject matter, the vectors of the presently-disclosed subject matter are viruses, such as a tobamoviruses (e.g., tobacco mosaic virus, turnip vein-clearing virus, tomato mosaic virus, etc.), cowpea mosaic virus, potato virus X, geminiviruses, among others, as such viruses have been found to be particularly useful for introducing a nucleic acid sequence of the presently-disclosed subject matter into a plant cell and for subsequently expressing the protein encoded by the nucleic acid in the plant cell.

In some embodiments, the isolated nucleic acid included in the vector is operably linked to an expression control sequence. The terms "associated with," "operably linked," and "operatively linked" refer to two nucleic acid sequences that are related physically or functionally. For example, a promoter or regulatory DNA sequence is said to be "associated with" a DNA sequence that encodes an RNA or a polypeptide if the two sequences are operatively linked, or situated such that the regulator DNA sequence will affect the expression level of the coding or structural DNA sequence.

The term "expression control sequence" refers to a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a nontranslated RNA, in the sense or antisense direction. The expression control sequence comprising the nucleotide sequence of interest can be chimeric, meaning that at least one of its components is heterologous with respect to at least one of its other components. The expression control sequence can also be one that is naturally occurring but has been obtained in a recombinant form useful for heterologous expression.

The presently-disclosed subject matter also provides transgenic plant cells or plants that have been transfected with one or more of the vectors disclosed herein. As used herein, the term "plant cell" is understood to mean any cell derived from a monocotyledonous or a dicotyledonous plant and capable of constituting undifferentiated tissues such as calli, differentiated tissues such as embryos, portions of monocotyledonous or dicotyledonous plants, monocotyledonous or dicotyledonous plants or seed. The term "plant" is understood to mean any differentiated multi-cellular organism capable of photosynthesis, including monocotyledons and dicotyledons. In some embodiments, the plant cell can be a tobacco plant cell, such as a *Nicotiana benthamiana* plant cell.

The terms "transformed," "transgenic," and "recombinant" are used herein to refer to a cell of a host organism, such as a plant, into which a heterologous nucleic acid molecule has been introduced. The nucleic acid molecule can be stably integrated into the genome of the cell or the nucleic acid molecule can also be present as an extrachromosomal molecule. Such an extrachromosomal molecule can be auto-replicating. Transformed cells, tissues, or subjects are understood to encompass not only the end product of a transformation process, but also transgenic progeny thereof.

The terms "heterologous," "recombinant," and "exogenous," when used herein to refer to a nucleic acid sequence (e.g., a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found. Similarly, when used in the context of a polypeptide or amino acid sequence, an exogenous polypeptide or amino acid sequence is a polypeptide or amino acid sequence that originates from a source foreign to the particular host cell or, if from the same source, is modified from its original form. Thus, exogenous DNA segments can be expressed to yield exogenous polypeptides.

Introduction of a nucleic acid (e.g., a nucleic acid incorporated into an appropriate vector) of the presently-disclosed subject matter into a plant cell can be performed by a variety of methods known to those of ordinary skill in the art including, but not limited to, insertion of a nucleic acid sequence of interest into an *Agrobacterium rhizogenes* Ri or *Agrobacterium tumefaciens* Ti plasmid, microinjection, electroporation, or direct precipitation. By way of providing an example, in some embodiments, transient expression of a nucleic acid sequence or gene of interest can be performed by agro-infiltration methods. In this regard, a suspension of *Agrobacterium tumefaciens* containing a nucleic acid sequence or gene of interest (e.g., due to electroporation) can be grown in culture and then a suspension of the bacterial culture can be infiltrated into the plant by applying a vacuum. Once inside the leaf, the *Agrobacterium* transforms the gene of interest to a portion of the plant cells where the gene is then expressed. For additional information and guidance regarding the expression of a nucleic acid sequence of interest in a plant cell, see, e.g., Matoba N, et al. Methods Mol Biol. 2011; 701:199-219; and, Matoba N, et al. PLoS One. 2010 Jun. 15; 5(6):e11143, each of which are incorporated herein by this reference.

For further guidance regarding methods of transforming and producing transgenic plant cells, see U.S. Pat. Nos. 4,459,355; 4,536,475; 5,464,763; 5,177,010; 5,187,073; 4,945,050; 5,036,006; 5,100,792; 5,371,014; 5,478,744; 5,179,022; 5,565,346; 5,484,956; 5,508,468; 5,538,877; 5,554,798; 5,489,520; 5,510,318; 5,204,253; 5,405,765; EP Nos. 267,159; 604,662; 672,752; 442,174; 486,233; 486,234; 539,563; 674,725; and, International Patent Application Publication Nos. WO 91/02071 and WO 95/06128, each of which is incorporated herein by this reference.

Still further provided, in some embodiments of the presently-disclosed subject matter are pharmaceutical compositions comprising a polypeptide of the presently-disclosed subject matter and a pharmaceutically-acceptable vehicle, carrier, or excipient. For example, in some embodiments, a pharmaceutical composition is provided that comprises: a polypeptide comprising an $AH_{var}$ polypeptide having an amino acid sequence selected from SEQ ID NOS: 4-12; and a pharmaceutically-acceptable vehicle, carrier, or excipient. As another example, in some embodiments, a pharmaceutical composition is provided that comprises a fusion protein of the presently-disclosed subject matter (e.g., a fusion protein comprising an $AH_{var}$ polypeptide having an amino acid sequence selected from SEQ ID NOS: 4-12, and a Fc, Fab, or scFV fragment of an antibody) and a pharmaceutically-acceptable vehicle, carrier, or excipient.

For example, solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, but are not limited to, microcrystalline cellulose, corn starch, sodium starch glycolate, and alginic acid. Tablet binders that can be used include acacia, methylcellulose, sodium carboxymethylcellulose, polyvinylpyrrolidone (POVIDONE™), hydroxypropyl methylcellulose, sucrose, starch, and ethylcellulose. Lubricants that can be used include magnesium stearates, stearic acid, silicone fluid, talc, waxes, oils, and colloidal silica. Further, the solid formulations can be uncoated or they can be coated by known techniques to delay disintegration and absorption in the gastrointestinal tract and thereby provide a sustained/extended action over a longer period of time. For example, glyceryl monostearate or glyceryl distearate can be employed to provide a sustained-/extended-release formulation. Numerous techniques for formulating sustained release preparations are known to those of ordinary skill in the art and can be used in accordance with the present invention, including the techniques described in the following references: U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921; 5,603,956; 5,512,297; 5,399,362; 5,399,359; 5,399,358; 5,725,883; 5,773,025; 6,110,498; 5,952,004; 5,912,013; 5,897,876; 5,824,638; 5,464,633; 5,422,123; and 4,839,177; and WO 98/47491, each of which is incorporated herein by this reference.

Furthermore, liquid formulations of the compositions for oral administration can be prepared in water or other aqueous vehicles, and can contain various suspending agents such as methylcellulose, alginates, tragacanth, pectin, kelgin, carrageenan, acacia, polyvinylpyrrolidone, and include solutions, emulsions, syrups, and elixirs containing, together with the active components of the composition, wetting agents, sweeteners, and coloring and flavoring agents.

Various liquid and powder formulations can also be prepared by conventional methods for inhalation into the lungs of the subject to be treated. For example, the compositions can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. Capsules and cartridges of, for example, gelatin for use in an inhaler or insufflator may be formulated containing a powder mix of the desired compound and a suitable powder base such as lactose or starch.

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol), and the like. For intravenous injections, water soluble versions of the compositions can be administered by the drip method, whereby a formulation including a pharmaceutical composition of the presently-disclosed subject matter and a physiologically-acceptable excipient is infused. Physiologically-acceptable excipients can include, for example, 5% dextrose, 0.9% saline, Ringer's solution or other suitable excipients. Intramuscular preparations, e.g., a sterile formulation of a suitable soluble salt form of the compositions, can be dissolved and administered in a pharmaceutical excipient such as Water-for-Injection, 0.9% saline, or 5% glucose solution. A suitable insoluble form of the compositions can be prepared and administered as a suspension in an aqueous base or a pharmaceutically-acceptable oil base, such as an ester of a long chain fatty acid, (e.g., ethyl oleate).

In addition to the formulations described above, the compositions of the presently-disclosed subject matter can also be formulated as rectal compositions, such as suppositories or retention enemas, e.g., containing conventional suppository bases such as cocoa butter or other glycerides. Further, the compositions can also be formulated as a depot preparation by combining the compositions with suitable polymeric or hydrophobic materials (for example as an emulsion in an acceptable oil) or ion exchange resins, or as sparingly soluble derivatives, for example, as a sparingly soluble salt.

In some embodiments of the present invention, the compositions of the present invention may be incorporated as part of a nanoparticle. A "nanoparticle" within the scope of the presently-disclosed subject matter is meant to include particles at the single molecule level as well as those aggregates of particles that exhibit microscopic properties. Methods of using and making a nanoparticle that incorporates a compound of interest are known to those of ordinary skill in the art and can be found following references: U.S. Pat. Nos. 6,395,253, 6,387,329, 6,383,500, 6,361,944, 6,350,515, 6,333,051, 6,323,989, 6,316,029, 6,312,731, 6,306,610, 6,288,040, 6,272,262, 6,268,222, 6,265,546, 6,262,129, 6,262,032, 6,248,724, 6,217,912, 6,217,901, 6,217,864, 6,214,560, 6,187,559, 6,180,415, 6,159,445, 6,149,868, 6,121,005, 6,086,881, 6,007,845, 6,002,817, 5,985,353, 5,981,467, 5,962,566, 5,925,564, 5,904,936, 5,856,435, 5,792,751, 5,789,375, 5,770,580, 5,756,264, 5,705,585, 5,702,727, and 5,686,113, each of which is incorporated herein by this reference.

A topical formulation (e.g., a semi-solid ointment formulation) can also be provided and can contain a desired concentration of the active ingredient (e.g., a polypeptide of the presently-disclosed subject matter) in a carrier such as a pharmaceutical cream base. Various formulations for topical use include drops, tinctures, lotions, creams, solutions, and ointments containing the active ingredient and various supports and vehicles. The optimal percentage of the therapeutic agent in each pharmaceutical formulation varies according to the formulation itself and the therapeutic effect desired in the specific pathologies and correlated therapeutic.

In yet further embodiments of the presently-disclosed subject matter, methods of treating a viral infection are provided. In some embodiments, a method of treating an infection of a subject by an enveloped virus is provided that includes administering an effective amount of a polypeptide of the presently-disclosed subject matter to the subject.

As used herein, the terms "treatment" or "treating" relate to any treatment of an infection of a subject by an enveloped virus, including but not limited to prophylactic treatment and therapeutic treatment. As such, the terms treatment or treating include, but are not limited to: preventing an enveloped viral infection or the development of an enveloped viral infection; inhibiting the progression of an enveloped viral infection; arresting or preventing the development of an enveloped viral infection; reducing the severity of an enveloped viral infection; ameliorating or relieving symptoms associated with an enveloped viral infection; and causing a regression of the enveloped viral infection or one or more of the symptoms associated with the enveloped viral infection.

The phrase "enveloped viral infection" is used herein to refer to any infection that is caused, at least in part, or exacerbated by the reproduction and proliferation of enveloped viruses within the body of a subject, including, but not limited to: the reproduction and proliferation of enveloped DNA viruses, such as herpesviruses, poxviruses, hepadnaviruses; the reproduction and proliferation of enveloped RNA viruses, such as flavivirus, togavirus, coronavirus, hepatitis D, orthomyxovirus, paramyxovirus, rhabdovirus, bunyavirus, filovirus; and the reproduction and proliferation of enveloped retroviruses, such as human immunodeficiency virus (HIV) and hepadnavirus. As noted herein, enveloped viruses are characterized by viral envelopes that cover the protein capsids of the viruses and are typically comprised of portions of the host cell lipid membranes and a number of glycoproteins that serve to identify and bind to receptor sites on the host cell membranes. It has been determined, however, that the administration of a polypeptide of the presently-disclosed subject matter (e.g., a fusion protein comprising an $AH_{var}$ polypeptide and an antibody fragment, such as an Fc fragment) to a subject is useful in the treatment of an enveloped viral infection, as defined herein. In particular, it has been determined that the polypeptides of the presently-disclosed subject matter are capable of binding to the outer glycoproteins of the envelopes found on enveloped viruses and are able to prevent or otherwise reduce the binding of the enveloped viruses to a host cell. As such, in some embodiments of the therapeutic methods described herein, the enveloped viruses are selected from a human immunodeficiency virus (HIV), an influenza virus, a hanta virus, a hepatitis C virus, a herpes virus, a severe acute respiratory syndrome coronavirus (SARS-CoV), a metapneumovirus, a henipavirus (e.g., Hendravirus and Nipahvirus), a flavivirus (e.g., Dengue and West Nile viruses) and a hemorrhagic fever virus (e.g., Marburg and Ebola viruses).

For administration of a therapeutic composition as disclosed herein, conventional methods of extrapolating human dosage based on doses administered to a murine animal model can be carried out using the conversion factor for converting the mouse dosage to human dosage: Dose Human per kg=Dose Mouse per kg×12 (Freireich, et al., (1966) Cancer Chemother Rep. 50:219-244). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/$m^2$.

Suitable methods for administering a therapeutic composition in accordance with the methods of the present invention include, but are not limited to, systemic administration, parenteral administration (including intravascular, intramuscular, intraarterial administration), oral delivery, topical administration, buccal delivery, rectal delivery, vaginal delivery, subcutaneous administration, intraperitoneal administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180,082). In some embodiments, such as those which include a pharmaceutical composition comprising a $AH_{var}$ polypeptide of the presently-disclosed subject matter, the pharmaceutical composition can be administered topically to thereby treat a viral infection.

Regardless of the route of administration, the compounds of the present invention are typically administered in amount effective to achieve the desired response. As used herein, the terms "effective amount" and "therapeutically effective amount" refer to an amount of the therapeutic composition (e.g., a composition comprising an $AH_{var}$ polypeptide, and a pharmaceutically vehicle, carrier, or excipient) sufficient to produce a measurable biological response (e.g., a decrease in the amount of an enveloped viral infection). Actual dosage levels of active ingredients in a therapeutic composition of the present invention can be varied so as to administer an amount of the active polypeptide(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902 and 5,234,933; PCT International Publication No. WO 93/25521; Berkow, et al., (1997) The Merck Manual of Medical Information, Home ed. Merck Research Laboratories, Whitehouse Station, N.J.; Goodman, et al., (2006) Goodman & Gilman's the Pharmacological Basis of Therapeutics, 11th ed. McGraw-Hill Health Professions Division, New York; Ebadi. (1998) CRC Desk Reference of Clinical Pharmacology. CRC Press, Boca Raton, Fla.; Katzung, (2007) Basic & Clinical Pharmacology, 10th ed. Lange Medical Books/McGraw-Hill Medical Pub. Division, New York; Remington, et al., (1990) Remington's Pharmaceutical Sciences, 18th ed. Mack Pub. Co., Easton, Pa.; Speight, et al., (1997) Avery's Drug Treatment: A Guide to the Properties, Choice, Therapeutic Use and Economic Value of Drugs in Disease Management, 4th ed. Adis International, Auckland/Philadelphia; and Duch, et al., (1998) Toxicol. Lett. 100-101:255-263, each of which are incorporated herein by reference.

As used herein, the term "subject" includes both human and animal subjects. Thus, veterinary therapeutic uses are provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples. Some of the following examples may include compilations of data that are representative of data gathered at various times during the course of development and experimentation related to the present invention. Additionally, certain of the following examples are prophetic, notwithstanding the numerical values, results and/or data referred to and contained in the examples.

EXAMPLES

Example 1

Generation of Actinohivin Variant ($AH_{var}$) Polypeptide

Due to observations of poor expression and poor solubility in aqueous buffer solutions when actinohivin (AH) polypeptides were expressed in plants, modifications to the AH polypeptide sequence were undertaken in an attempt to increase the expression of the polypeptides in plants and to increase the solubility of the polypeptides. Without wishing to be bound by any particular theory, it was believed that one of the causes of the low expression of the AH polypeptides was due to AH's relatively high isoelectric point (greater than 8). As such, an initial modification to the amino acid sequence changed the glutamine residue at the sixth position within the first and second carbohydrate-binding domains of the AH polypeptide to glutamic acid, such that the glutamic acid residues in the sixth position of the first and second carbohydrate-binding domains corresponded to the glutamic acid residue in the third carbohydrate binding domain of the AH polypeptide. Also without wishing to be bound by any particular theory, it was further believed that the poor expression was due to the poor stability of the AH polypeptide and, as such, the first and third carbohydrate-binding domains were further modified such that the produced variant proteins would include two cysteine residues that would then facilitate the formation of an intra-domain disulfide bond, such as what is found in the second carbohydrate-binding domain. To further improve the solubility, it was also believed that it was necessary to reduce the hydrophobicity of the protein and, to this end, the second hinge region of AH was modified to resemble the first hinge region, as the former contained very hydrophobic residues such as leucine and phenylalanine, whereas the latter was more charged and was thus more hydrophilic. For a comparison of the native AH polypeptide with the initially constructed AH variant polypeptide (i.e., $AH_{var1}$ polypeptide), see, e.g., FIGS. 1A and 1B.

Following the design of the modified AH polypeptide ($AH_{var1}$; SEQ ID NO: 4), a nucleic acid sequence (SEQ ID NO: 3) encoding the modified polypeptide was then synthesized and the $AH_{var1}$ polypeptide was subsequently expressed in *Nicotiana benthamiana* using the magnICON system (Icon Genetics Inc., Halle/Saale, Germany), where the nucleic acid sequence encoding the $AH_{var1}$ polypeptide was cloned into a pICH11599 vector, both with a signal peptide to target the $AH_{var1}$ polypeptide to the endomembrane system (EMS) and without a signal peptide to allow for cytosolic expression of the polypeptide. Upon analysis of the *Nicotiana benthamiana* expressing these polypeptides, and as shown in FIG. 2, it was found that $AH_{var1}$ polypeptides were highly-expressed in the plant tissues as compared to the levels of native AH polypeptides that were expressed in the same tissues, indicating that the amino acid modifications improved the expression of the polypeptide in plant tissues.

Example 2

Figure 3:
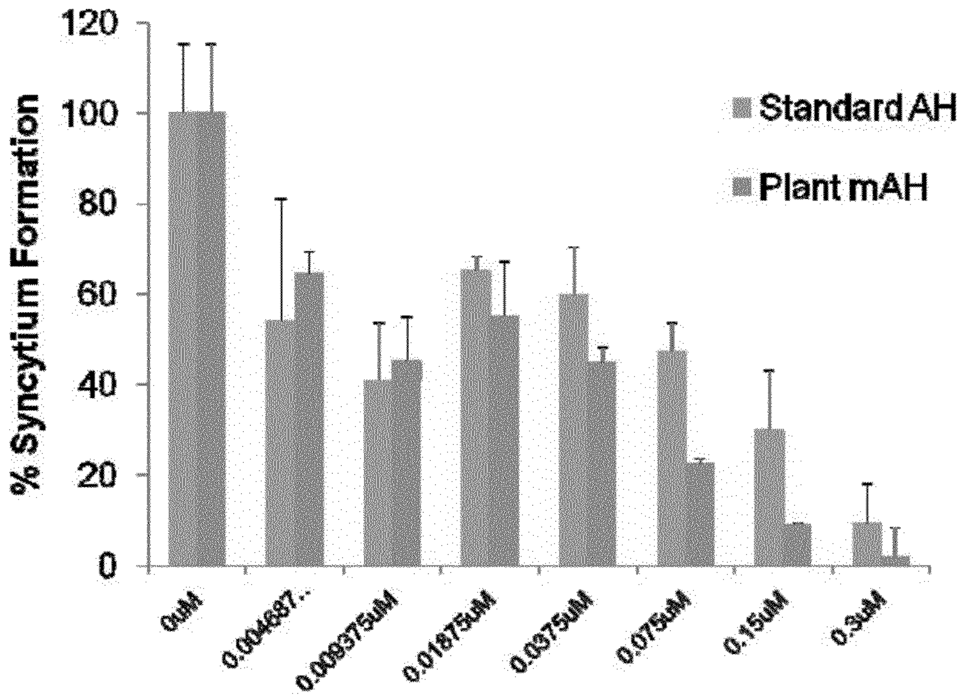
FIG. 3 is a graph showing the results of an Env-$CD_4$ syncytium formation assay used to measure the anti-human immunodeficiency virus (HIV) activity of an $AH_{var1}$ polypeptide, where the percent of syncytium formation is plotted against the concentrations of the polypeptides used in the assay, and where the results obtained with particular concentrations of the $AH_{var1}$ polypeptide (Plant mAH) are plotted along with the results obtained using the same concentrations of native AH (Standard AH)

Anti-Human Immunodeficiency Virus Activity of Actinohivin Variant ($AH_{var}$) Polypeptide To further assess the properties of the $AH_{var1}$ polypeptide and, in particular to assess the ability of the $AH_{var1}$ polypeptide to display anti-human immunodeficiency virus (HIV) activity, a syncytium formation assay was performed using HeLa/env/tat and HeLa/CD4/lacZ cell lines as previously described in Matoba et al. PLoS ONE, 2010. Briefly, in 96-well plates, serially-diluted, clarified leaf extracts, either in PBS for the $AH_{var1}$ polypeptide or in 2% SDS for native AH, were mixed with 9,000 cells/well of the two cell lines and were incubated for 18 hrs at 37° C. The syncytium formation was then quantified by beta-galactosidase activity of cell lysates. As shown in FIG. 3, upon analysis of the results from these experiments, it was found that the $AH_{var1}$ polypeptide (Plant mAH) was able to reduce the percentage of syncytiums formed, thus indicating that the $AH_{var1}$ polypeptide is useful for treating an enveloped virus infection.

Example 3

Generation, Expression, and Activity of Additional Actinohivin Variant ($AH_{var}$) Polypeptides Based on the results obtained with the initial $AH_{var1}$ polypeptide, 8 additional AH variant polypeptide were designed and tested. Each of these AH variant polypeptides ($AH_{var2-9}$ polypeptides; SEQ ID NOS: 5-12) were observed to be capable of expression in plants. Additionally, each of the further variant polypeptides are shown to be capable of reducing the percentage of syncytiums formed in an Env-$CD_4$ syncytium formation assay, indicating that the further AH variant polypeptides found in SEQ ID NOS: 5-12 are also useful for treating an enveloped virus infection.

Example 4

Figure 4:
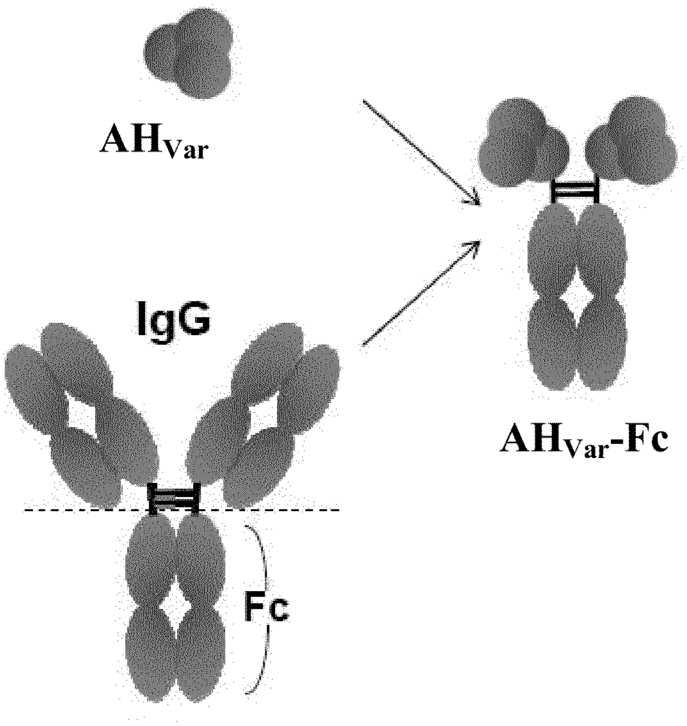
FIG. 4 is a schematic representation of an $AH_{var}$-Fc fusion protein of the presently-disclosed subject matter.
Figure 5:
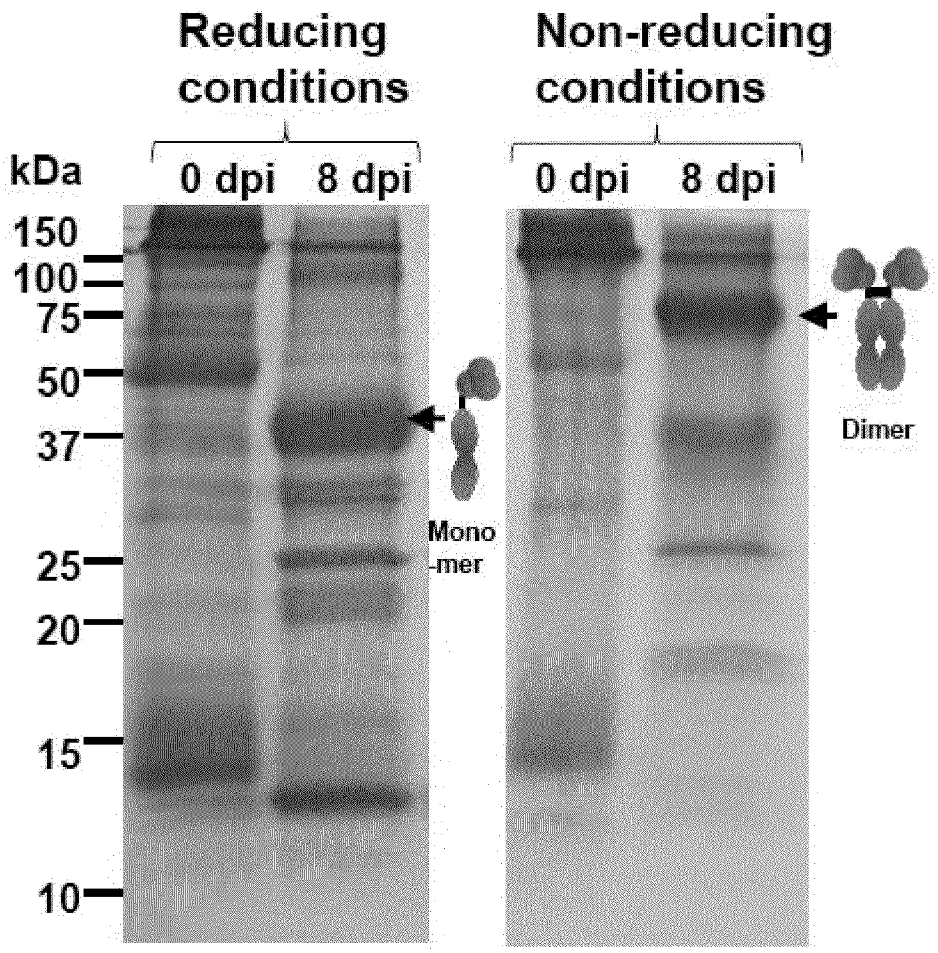
FIG. 5 includes images of gels showing the SDS-PAGE analysis of an $AH_{var1}$ polypeptide produced in *Nicotiana benthamiana* plants under reducing condition and non-reducing conditions at 8 days post vector inoculation (dpi)

Generation and Expression of Actinohivin Variant ($AH_{var}$) Fusion Protein To examine whether combining the $AH_{var1}$ polypeptide with an antibody fragment would further improve the properties of the $AH_{var1}$ polypeptide, an $AH_{var1}$ polypeptide-Fc fusion protein was constructed by attaching the nucleic acid sequence encoding for the hinge and the Fc region of a human immunoglobulin (Ig)G to the 3' end of the $AH_{var1}$ polypeptide-coding sequence via a flexible peptide linker (Gly-Gly-Gly-Ser; SEQ ID NO: 13) coding sequence to potentially improve the antiviral activity of the fusion proteins (see, e.g., FIG. 4). In addition, a DNA sequence coding for an endomembrane system (EMS)-targeting signal peptide derived from rice alpha-amylase was attached to the 5' end of the $AH_{var1}$ polypeptide-coding sequence to direct the expression of the $AH_{var1}$ polypeptide to the plant's EMS. Without wishing to be bound by any particular theory, it was believed that the $AH_{var1}$ polypeptide could be produced as part of a Fc fusion protein, as well as an Fab and scFv antibody fusion protein, due to the finding that the $AH_{var1}$ polypeptide was highly expressed in the apoplast via the plant cell's EMS (i.e., the endoplasmic reticulum and the Golgi apparatus) where antibody fragments are properly assembled into functional molecules, while, other well-known high-mannose-glycan-specific anti-HIV lectins, such as griffithsin and cyanovirin-N, do not appear to be compatible with EMS-based high expression Once the nucleic acid sequence for the $AH_{var1}$ polypeptide-Fc fusion protein was designed and constructed, a "deconstructed" tobamovirus replicon system (magnICON; Icon Genetics GmbH, Halle/Saale, Germany) was then used to express the $AH_{var1}$ polypeptide-Fc fusion protein in *N. benthamiana*. Briefly, the $AH_{var1}$ polypeptide-Fc fusion protein-coding DNA sequence was sub-cloned into the vector pICH38099, and the plasmid was transferred into the *Agrobacterium tumefaciens* strain GV3101 by electroporation. The bacteria were then resuspended in an infiltration buffer (10 mM 2-(N-morpholino)ethanesulphonic acid [MES], 10 mM $MgSO_4$, pH 5.5) to give an optical density at 600 nm (OD600) of 0.03. The *N. benthamiana* plants were grown at 27° C. and 55 to 65% humidity for 4 weeks under an 18 h-light/6 h-dark cycle, and the bacteria suspension was subsequently infiltrated into leaves by application of a vacuum for 2 min at 25 inches Hg using a vacuum pump. After infiltration, the plants were placed in the growth chamber set at the same conditions described above. At 7 days post infiltration, infected leaves were then harvested and examined for $AH_{var1}$ polypeptide-Fc fusion protein expression by SDS-PAGE (FIG. 5). The protein was detected at a predicted size of approximately 37 kilodaltons and was expressed at a very high level, reaching 2 to 3 g per kg of leaf material. SDS-PAGE analysis under non-reducing conditions (without 2-mercaptoethanol in the sample buffer) revealed that the majority of the expressed protein forms a dimer via disulfide bonding like immunoglobulins. Western blot analysis further confirmed that the expressed protein possessed both $AH_{var1}$ polypeptide and Fc domains. The *Nicotiana*-expressed $AH_{var1}$ polypeptide-Fc fusion protein's ability to bind to HIV gp120 was further demonstrated by gp120-capture enzyme-linked immunosorbent assay (gp120-ELISA). The protein was then extracted and purified using a Protein G column for further analysis.

Without wishing to be bound by any particular theory, and based on the results obtained with an $AH_{var1}$ polypeptide-Fc fusion protein, it is believed that other $AH_{var1}$ polypeptide-immunoglobulin fusions can be developed in a similar fashion, including $AH_{var1}$ polypeptide-Fab and $AH_{var1}$ polypeptide-scFv fusion proteins. More specifically, it is believed that Fab and scFv molecules can be attached to either or both the N- and/or C-termini of the $AH_{var1}$ polypeptide because the crystal structure of AH (Protein Data Bank ID: 3a07) revealed that both the N- and C-termini are exposed and located away from the putative carbohydrate-binding pockets of the lectin.

Example 5

Figure 6:
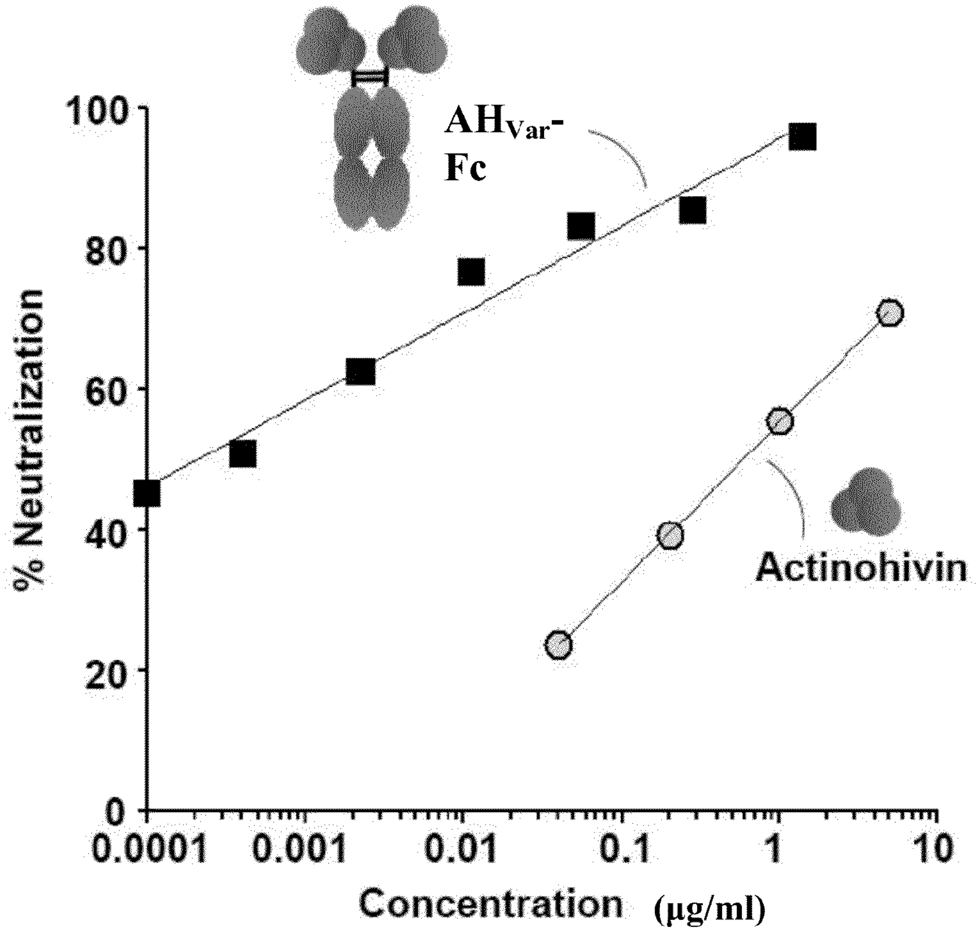
FIG. 6 is a graph showing the results of an in vitro HIV neutralization assay where the percent of HIV neutralization is plotted as a function of the concentration of $AH_{var}$-Fc fusion polypeptide or actinohivin (AH) polypeptide used in the assay.

Anti-Human Immunodeficiency Virus Activity of Actinohivin Variant ($AH_{var}$) Fusion Protein To further examine the properties of the $AH_{var1}$ polypeptide-Fc fusion protein, the antiviral activity of AH and the $AH_{var1}$ polypeptide-Fc fusion protein was assessed based on a reduction in luciferase reporter gene expression after infection of TZM-bl cells with HIV envelope (Env)-pseudotyped viruses. The assay was performed as described in: Matoba et al. PLoS ONE 2010 e11143, with antiviral activity being expressed as a percentage of neutralization, and where an average relative luminescence unit (RLU) obtained at each concentration of the $AH_{var1}$ polypeptide-Fc fusion protein was compared with that of the virus control after subtraction of background RLUs. Briefly, Env-pseudotyped viruses were prepared by co-transfection of 293T/17 cells with a MN strain's env-expressing plasmid and an env-deficient HIV-1 backbone vector (pSG3ΔEnv). Samples and the virus were mixed and incubated for 1 h at 37° C., to which $10^4$ cells/well of TZM-bl cells were added and incubated for 72 h. Luciferase activity of the cell lysates was then measured using a plate reader. Upon analysis of the results from the assay, it was observed that AH dose-dependently neutralized the virus with a 50% inhibitory concentration ($IC_{50}$) of approximately 0.5 μg/ml (FIG. 6; Actinohivin). The $AH_{var1}$ polypeptide-Fc fusion protein, however, exhibited a much more potent activity, with an $IC_{50}$ of less than 0.001 μg/ml (FIG. 6; $AH_{var}$-Fc), indicating that the fusion of the $AH_{var1}$ polypeptide to an IgG Fc fragment enhances the anti-HIV activity of the variant polypeptide, while possibly also providing additional efficacy via various Fc-mediated biological functions, such as antibody-dependent cell-mediated cytotoxicity, complement-dependent cytotoxicity, antibody-dependent cellular phagocytosis, antibody-dependent cell-mediated virus inhibition, as well as a long serum half life upon systemic use (see, e.g., Forthal et al., Curr Opin HIV AIDS 2009, 4; 388-393; Moore et al., mAbs 2010, 2; 18-189, see also, e.g., Hansel et al., Nat Rev Drug Discov 2010; 9(4):325-38; and Moore et al., mAbs 2010, 2; 18-189, describing how manipulation of Fc-mediated activities (e.g., augmentation, reduction, or elimination) can be achieved by modifying the Fc sequence, each of which are incorporated herein by reference).

Throughout this document, various references are mentioned. All such references are incorporated herein by reference, including the references set forth in the following list:

REFERENCES

1. AIDS epidemic update. AIDS epidemic update: 2009. Joint United Nations Programme on HIV/AIDS & World Health Organization.
2. Garg A B, Nuttall J, Romano J. The future of HIV microbicides: challenges and opportunities. Antivir Chem Chemother. 2009; 19:143-150.

3. McGowan I. Microbicides for HIV prevention: reality or hope? Curr Opin Infect Dis. 2010; 23:26-31.
4. Morris G C, Lacey C J. Microbicides and HIV prevention: lessons from the past, looking to the future. Curr Opin Infect Dis. 2010; 23: 57-63.
5. Grant R M, Hamer D, Hope T, Johnston R, Lange J, et al. Whither or wither microbicides? Science. 2008; 321:532-534.
6. Scanlan C N, Offer J, Zitzmann N, Dwek R A. Exploiting the defensive sugars of HIV-1 for drug and vaccine design. Nature. 2007; 446:1038-1045.
7. Balzarini J. Targeting the glycans of glycoproteins: a novel paradigm for antiviral therapy. Nat Rev Microbiol. 2007; 5:583-597.
8. Swanson M D, Winter H C, Goldstein I J, Markovitz D M. A lectin isolated from bananas is a potent inhibitor of HIV replication. J Biol Chem 2010
9. Calarese D A, Lee H K, Huang C Y, Best M D, Astronomo R D, et al. Dissection of the carbohydrate specificity of the broadly neutralizing anti-HIV-1 antibody 2G12. Proc Natl Acad Sci USA. 2005; 102:13372-13377.
10. Scanlan C N, Pantophlet R, Wormald M R, Ollmann Saphire E, Stanfield R, et al. The broadly neutralizing anti-human immunodeficiency virus type 1 antibody 2G12 recognizes a cluster of alpha1-->2 mannose residues on the outer face of gp120. J Virol. 2002; 76:7306-7321.
11. Chiba H, Inokoshi J, Okamoto M, Asanuma S, Matsuzaki K, et al. Actinohivin, a novel anti-HIV protein from an actinomycete that inhibits syncytium formation: isolation, characterization, and biological activities. Biochem Biophys Res Commun. 2001; 282:595-601.
12. Tanaka H, Chiba H, Inokoshi J, Kuno A, Sugai T, et al. Mechanism by which the lectin actinohivin blocks HIV infection of target cells. Proc Natl Acad Sci USA. 2009; 106:15633-15638.
13. Takahashi A, Inokoshi J, Chiba H, Omura S, Tanaka H. Essential regions for antiviral activities of actinohivin, a sugar-binding anti-human immunodeficiency virus protein from an actinomycete. Arch Biochem Biophys. 2005; 437: 233-240.
14. Lin G, Simmons G, Pohlmann S, Baribaud F, Ni H, et al. Differential N-linked glycosylation of human immunodeficiency virus and Ebola virus envelope glycoproteins modulates interactions with DC-SIGN and DC-SIGNR. J Virol. 2003; 77:1337-1346.
15. Chiba H, Inokoshi J, Nakashima H, Omura S, Tanaka H. Actinohivin, a novel anti-human immunodeficiency virus protein from an actinomycete, inhibits viral entry to cells by binding high-mannose type sugar chains of gp120. Biochem Biophys Res Commun. 2004; 316:203-210.
16. Fenyo E M, Heath A, Dispinseri S, Holmes H, Lusso P, et al. International network for comparison of HIV neutralization assays: the NeutNet report. PLoS ONE. 2009; 4:e4505.
17. D'Souza M P, Milman G, Bradac J A, McPhee D, Hanson C V, et al. Neutralization of primary HIV-1 isolates by anti-envelope monoclonal antibodies. Aids. 1995; 9:867-874.
18. Mascola J R, Louder M K, Surman S R, Vancott T C, Yu X F, et al. Human immunodeficiency virus type 1 neutralizing antibody serotyping using serum pools and an infectivity reduction assay. AIDS Res Hum Retroviruses. 1996; 12:1319-1328.
19. Wang C Y, Sawyer L S, Murthy K K, Fang X, Walfield A M, et al. Postexposure immunoprophylaxis of primary isolates by an antibody to HIV receptor complex. Proc Natl Acad Sci USA. 1999; 96:10367-10372.
20. Elrefaei M, McElroy M D, Preas C P, Hoh R, Deeks S, et al. Central memory CD4+ T cell responses in chronic HIV infection are not restored by antiretroviral therapy. J Immunol. 2004; 173:2184-2189.
21. Fraser J D, Proft T. The bacterial superantigen and superantigen-like proteins. Immunol Rev. 2008; 225:226-243.
22. Montefiori D C. Measuring HIV neutralization in a luciferase reporter gene assay. Methods Mol Biol. 2009; 485:395-405.
23. Zhang M, Gaschen B, Blay W, Foley B, Haigwood N, et al. Tracking global patterns of N-linked glycosylation site variation in highly variable viral glycoproteins: HIV, SIV, and HCV envelopes and influenza hemagglutinin. Glycobiology. 2004; 14:1229-1246.
24. Marillonnet S, Giritch A, Gils M, Kandzia R, Klimyuk V, et al. In planta engineering of viral RNA replicons: efficient assembly by recombination of DNA modules delivered by *Agrobacterium*. Proc Natl Acad Sci USA. 2004; 101:6852-6857.
25. Marillonnet S, Thoeringer C, Kandzia R, Klimyuk V, Gleba Y. Systemic *Agrobacterium tumefaciens*-mediated transfection of viral replicons for efficient transient expression in plants. Nat Biotechnol. 2005; 23:718-723.
26. Chiba H, Asanuma S, Okamoto M, Inokoshi J, Tanaka H, et al. A simple screening system for anti-HIV drugs: syncytium formation assay using T-cell line tropic and macrophage tropic HIV env expressing cell lines—establishment and validation. J Antibiot (Tokyo) 2001; 54:818-826.
27. Sharon N, Lis H. History of lectins: from hemagglutinins to biological recognition molecules. Glycobiology. 2004; 14:53R-62R.
28. Gavrovic-Jankulovic M, Poulsen K, Brckalo T, Bobic S, Lindner B, et al. A novel recombinantly produced banana lectin isoform is a valuable tool for glycoproteomics and a potent modulator of the proliferation response in CD3+, CD4+, and CD8+ populations of human PBMCs. Int J Biochem Cell Biol. 2008; 40:929-941.
29. Huskens D, Vermeire K, Vandemeulebroucke E, Balzarini J, Schols D. Safety concerns for the potential use of cyanovirin-N as a microbicidal anti-HIV agent. Int J Biochem Cell Biol. 2008; 40:2802-2814.
30. Balzarini J, Van Laethem K, Peumans W J, Van Damme E J, Bolmstedt A, et al. Mutational pathways, resistance profile, and side effects of cyanovirin relative to human immunodeficiency virus type 1 strains with N-glycan deletions in their gp120 envelopes. J Virol. 2006; 80:8411-8421.
31. Lederman M M, Jump R, Pilch-Cooper H A, Root M, Sieg S F. Topical application of entry inhibitors as "virustats" to prevent sexual transmission of HIV infection. Retrovirology. 2008; 5:116.
32. Pope M, Haase A T. Transmission, acute HIV-1 infection and the quest for strategies to prevent infection. Nat Med. 2003; 9:847-852.
33. Taylor B S, Sobieszczyk M E, McCutchan F E, Hammer S M. The challenge of HIV-1 subtype diversity. N Engl J Med. 2008; 358:1590-1602.
34. Buonaguro L, Tornesello M L, Buonaguro F M. Human immunodeficiency virus type 1 subtype distribution in the worldwide epidemic: pathogenetic and therapeutic implications. J Virol. 2007; 81:10209-10219.
35. Calarese D A, Scanlan C N, Zwick M B, Deechongkit S, Mimura Y, et al. Antibody domain exchange is an immunological solution to carbohydrate cluster recognition. Science. 2003; 300:2065-2071.
36. Inokoshi J, Chiba H, Asanuma S, Takahashi A, Omura S, et al. Molecular cloning of actinohivin, a novel anti-HIV protein from an actinomycete, and its expression in *Escherichia coli*. Biochem Biophys Res Commun. 2001; 281:1261-1265.
37. Polonis V R, Brown B K, Rosa Borges A, Zolla-Pazner S, Dimitrov D S, et al. Recent advances in the characterization of HIV-1 neutralization assays for standardized evaluation of the antibody response to infection and vaccination. Virology. 2008; 375:315-320.
38. Keller M J, Herold B C. Understanding basic mechanisms and optimizing assays to evaluate the efficacy of vaginal microbicides. Sex Transm Dis. 2009; 36:S92-95.
39. Willey R L, Shibata R, Freed E O, Cho M W, Martin M A. Differential glycosylation, virion incorporation, and sensitivity to neutralizing antibodies of human immunodeficiency virus type 1 envelope produced from infected primary T-lymphocyte and macrophage cultures. J Virol. 1996; 70:6431-6436.
40. Liedtke S, Geyer R, Geyer H. Host-cell-specific glycosylation of HIV-2 envelope glycoprotein. Glycoconj J. 1997; 14:785-793.
41. Yuste E, Reeves J D, Doms R W, Desrosiers R C. Modulation of Env content in virions of simian immunodeficiency virus: correlation with cell surface expression and virion infectivity. J Virol. 2004; 78:6775-6785.
42. Bachrach E, Dreja H, Lin Y L, Mettling C, Pinet V, et al. Effects of virion surface gp120 density on infection by HIV-1 and viral production by infected cells. Virology. 2005; 332:418-429.
43. Peters P J, Sullivan W M, Duenas-Decamp M J, Bhattacharya J, Ankghuambom C, et al. Non-macrophage-tropic human immunodeficiency virus type 1 R5 envelopes predominate in blood, lymph nodes, and semen: implications for transmission and pathogenesis. J Virol. 2006; 80:6324-6332.
44. Paranjpe S, Craigo J, Patterson B, Ding M, Barroso P, et al. Subcompartmentalization of HIV-1 quasispecies between seminal cells and seminal plasma indicates their origin in distinct genital tissues. AIDS Res Hum Retroviruses. 2002; 18:1271-1280.
45. O'Keefe B R, Vojdani F, Buffa V, Shattock R J, Montefiori D C, et al. Scaleable manufacture of HIV-1 entry inhibitor griffithsin and validation of its safety and efficacy as a topical microbicide component. Proc Natl Acad Sci USA 2009.
46. Zhu X, Borchers C, Bienstock R J, Tomer K B. Mass spectrometric characterization of the glycosylation pattern of HIV-gp120 expressed in CHO cells. Biochemistry. 2000; 39:11194-11204.
47. Leonard C K, Spellman M W, Riddle L, Harris R J, Thomas J N, et al. Assignment of intrachain disulfide bonds and characterization of potential glycosylation sites of the type 1 recombinant human immunodeficiency virus envelope glycoprotein (gp120) expressed in Chinese hamster ovary cells. J Biol Chem. 1990; 265:10373-10382.
48. Cutalo J M, Deterding U, Tomer K B. Characterization of glycopeptides from HIV-I(SF2) gp120 by liquid chromatography mass spectrometry. J Am Soc Mass Spectrom. 2004; 15:1545-1555.
49. Shenoy S R, Barrientos L G, Ratner D M, O'Keefe B R, Seeberger P H, et al. Multisite and multivalent binding between cyanovirin-N and branched oligomannosides: calorimetric and NMR characterization. Chem Biol. 2002; 9:1109-1118.
50. Botos I, O'Keefe B R, Shenoy S R, Cartner L K, Ratner D M, et al. Structures of the complexes of a potent anti-HIV protein cyanovirin-N and high mannose oligosaccharides. J Biol Chem. 2002; 277:34336-34342.
51. Tsai C C, Emau P, Jiang Y, Tian B, Morton W R, et al. Cyanovirin-N gel as a topical microbicide prevents rectal transmission of SHIV89.6P in macaques. AIDS Res Hum Retroviruses. 2003; 19:535-541.
52. Tsai C C, Emau P, Jiang Y, Agy M B, Shattock R J, et al. Cyanovirin-N inhibits AIDS virus infections in vaginal transmission models. AIDS Res Hum Retroviruses. 2004; 20:11-18.
53. Buffa V, Stieh D, Mamhood N, Hu Q, Fletcher P, et al. Cyanovirin-N potently inhibits human immunodeficiency virus type 1 infection in cellular and cervical explant models. J Gen Virol. 2009; 90:234-243.
54. Zeitlin L, Pauly M, Whaley K J. Second-generation HIV microbicides: continued development of griffithsin. Proc Natl Acad Sci USA. 2009; 106:6029-6030.
55. Ma J K, Chikwamba R, Sparrow P, Fischer R, Mahoney R, et al. Plant-derived pharmaceuticals—the road forward. Trends Plant Sci. 2005; 10:580-585.
56. Matoba N, Davis K R, Palmer K E. Recombinant Protein Expression in *Nicotiana*. Methods Mol Biol. 2011; 701: 199-219.
57. Matoba N, Kajiura H, Cherni I, Doran J D, Bomsel M, et al. Biochemical and immunological characterization of the plant-derived candidate human immunodeficiency virus type 1 mucosal vaccine CTB-MPR(649-684). Plant Biotechnol J. 2009; 7:129-145.
58. Alouf J E, Muller-Alouf H. Staphylococcal and streptococcal superantigens: molecular, biological and clinical aspects. Int J Med Microbiol. 2003; 292:429-440.
59. Matoba N, Husk A S, Barnett B W, Pickel M M, et al. HIV-1 neutralization profile and plant-based recombinant expression of actinohivin, an Env glycan-specific lectin devoid of T-cell mitogenic activity. PLoS One. 2010 Jun. 15; 5(6):e11143.
60. U.S. Patent Application Publication No. 2009/0297516.
61. Takahashi A, et al. The high mannose-type glycan binding lectin actinohivin: dimerization greatly improves anti-HIV activity. J Antibiot. (Tokyo), 2011, Epub ahead of print.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of treating an infection of a subject by an enveloped virus, comprising administering to the subject an effective amount of an actinohivin variant polypeptide having an amino acid sequence selected from SEQ ID NOS: 4-12.

2. The method of claim 1, wherein the enveloped virus is selected from a human immunodeficiency virus (HIV), an influenza virus, a hanta virus, a hepatitis C virus, a herpes virus, a severe acute respiratory syndrome coronavirus (SARS-CoV), a metapneumovirus, a henipavirus, a flavivirus, and a hemorrhagic fever virus.

3. The method of claim 2, wherein the enveloped virus is HIV.

4. The method of claim 1, wherein administering the actinohivin variant polypeptide comprises topically administering the actinohivin variant polypeptide.

5. The method of claim 1, wherein the actinohivin variant polypeptide comprises the amino acid sequence of SEQ ID NO: 4.

6. The method of claim 1, further comprising administering a second polypeptide selected from: a fragment crystallizable domain of an antibody (Fc); a fragment antigen-binding domain of an antibody (Fab); and a single chain variable fragment of an antibody (scFv), wherein the actinohivin variant polypeptide and the second polypeptide comprise a fusion protein.

7. The method of claim 6, wherein the antibody is a monoclonal antibody.

8. The method of claim 6, wherein the second polypeptide is Fab.

9. The method of claim 6, wherein the second polypeptide is scFv.

10. The method of claim 6, wherein the second polypeptide is Fc.

11. The method of claim 6, wherein the polypeptide further comprises a peptide linker for connecting the actinohivin variant polypeptide to the second polypeptide.

12. The method of claim 11, wherein the peptide linker comprises an amino acid sequence of SEQ ID NO: 13.

13. A method of treating an infection of a subject by an enveloped virus, comprising administering to the subject an effective amount of:

a first polypeptide comprising an actinohivin variant polypeptide having an amino acid sequence selected from SEQ ID NOS: 4-12; and a second polypeptide selected from the group consisting of a fragment crystallizable domain of an antibody (Fc), a fragment antigen-binding domain of an antibody (Fab), and a single chain variable fragment of an antibody (scFv), wherein the first polypeptide and the second polypeptide comprise a fusion protein.

14. The method of claim 13, wherein the polypeptide further comprises a peptide linker for connecting the actinohivin variant polypeptide to the second polypeptide.

15. The method of claim 14, wherein the peptide linker comprises an amino acid sequence of SEQ ID NO: 13.

* * * * *

SEQUENCE LISTING

```
<160> NUMBER OF SEQ ID NOS: 15

<210> SEQ ID NO 1
<211> LENGTH: 345
<212> TYPE: DNA
<213> ORGANISM: Longispora albida

<400> SEQUENCE: 1
```

-continued

```
gcctcggtga ccatccgcaa cgcccagacc ggccgcctgc tggacagcaa ctacaacggc     60

aacgtctaca cgctgcccgc caacggcggg aactaccagc ggtggaccgg ccccggcgac    120

ggcaccgtcc gcaacgccca gaccggccgc tgcctcgaca gcaactacga cggcgccgtc    180

tacacgctgc cgtgcaacgg cggtagctac cagaagtggc tgttctacag caacggctac    240

atccagaacg tcgagaccgg acgcgtgctc gacagcaact acaacggcaa cgtgtacaca    300

ctgccggcca acggcggcaa ctaccagaag tggtacaccg gctaa                    345
```

```
<210> SEQ ID NO 2
<211> LENGTH: 114
<212> TYPE: PRT
<213> ORGANISM: Longispora albida

<400> SEQUENCE: 2

Ala Ser Val Thr Ile Arg Asn Ala Gln Thr Gly Arg Leu Leu Asp Ser
1               5                   10                  15

Asn Tyr Asn Gly Asn Val Tyr Thr Leu Pro Ala Asn Gly Gly Asn Tyr
            20                  25                  30

Gln Arg Trp Thr Gly Pro Gly Asp Gly Thr Val Arg Asn Ala Gln Thr
        35                  40                  45

Gly Arg Cys Leu Asp Ser Asn Tyr Asp Gly Ala Val Tyr Thr Leu Pro
    50                  55                  60

Cys Asn Gly Gly Ser Tyr Gln Lys Trp Leu Phe Tyr Ser Asn Gly Tyr
65                  70                  75                  80

Ile Gln Asn Val Glu Thr Gly Arg Val Leu Asp Ser Asn Tyr Asn Gly
                85                  90                  95

Asn Val Tyr Thr Leu Pro Ala Asn Gly Gly Asn Tyr Gln Lys Trp Tyr
            100                 105                 110

Thr Gly
```

```
<210> SEQ ID NO 3
<211> LENGTH: 342
<212> TYPE: DNA
<213> ORGANISM: Artificial Sequence
<220> FEATURE:
<223> OTHER INFORMATION: Actinohivin Variant Polypeptide

<400> SEQUENCE: 3

gcctcgggta ccatccgcaa cgccgaaacc ggccgctgtc tggacagcaa ctacaacggc     60

aacgtctaca cgctgccctg taacggcggg aactaccagc ggtggaccgg ccccggcgac    120

ggtaccgttc gcaacgccga aaccggccgc tgcctcgaca gcaactacga cggcgctgtc    180

tacacgctgc cgtgcaacgg cggtagctac cagaagtgga ctggtccagg tgacggcacc    240

atccagaacg cagagactgg acgctgtctc gacagcaact acaacggcaa cgtctacaca    300

ctgccgtgta acggcggcaa ctaccagaag tggaccggct aa                       342
```

```
<210> SEQ ID NO 4
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 4

Ala Ser Gly Thr Ile Arg Asn Ala Glu Thr Gly Arg Cys Leu Asp Ser
1               5                   10                  15
```

-continued

```
Asn Tyr Asn Gly Asn Val Tyr Thr Leu Pro Cys Asn Gly Gly Asn Tyr
            20                  25                  30

Gln Arg Trp Thr Gly Pro Gly Asp Gly Thr Val Arg Asn Ala Glu Thr
        35                  40                  45

Gly Arg Cys Leu Asp Ser Asn Tyr Asp Gly Ala Val Tyr Thr Leu Pro
    50                  55                  60

Cys Asn Gly Gly Ser Tyr Gln Lys Trp Thr Gly Pro Gly Asp Gly Thr
65                  70                  75                  80

Ile Gln Asn Ala Glu Thr Gly Arg Cys Leu Asp Ser Asn Tyr Asn Gly
                85                  90                  95

Asn Val Tyr Thr Leu Pro Cys Asn Gly Gly Asn Tyr Gln Lys Trp Thr
            100                 105                 110

Gly


<210> SEQ ID NO 5
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 5

Ala Ser Gly Thr Ile Arg Asn Ala Glu Thr Gly Arg Cys Leu Asp Ser
1               5                   10                  15

Asn Tyr Asp Gly Ala Val Tyr Thr Leu Pro Cys Asn Gly Gly Ser Tyr
            20                  25                  30

Gln Arg Trp Thr Gly Pro Gly Asp Gly Thr Val Arg Asn Ala Glu Thr
        35                  40                  45

Gly Arg Cys Leu Asp Ser Asn Tyr Asp Gly Ala Val Tyr Thr Leu Pro
    50                  55                  60

Cys Asn Gly Gly Ser Tyr Gln Lys Trp Thr Gly Pro Gly Asp Gly Thr
65                  70                  75                  80

Ile Gln Asn Ala Glu Thr Gly Arg Cys Leu Asp Ser Asn Tyr Asp Gly
                85                  90                  95

Ala Val Tyr Thr Leu Pro Cys Asn Gly Gly Ser Tyr Gln Lys Trp Thr
            100                 105                 110

Gly


<210> SEQ ID NO 6
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 6

Ala Ser Gly Thr Ile Arg Asn Ala Glu Thr Gly Arg Leu Leu Asp Ser
1               5                   10                  15

Asn Tyr Asp Gly Ala Val Tyr Thr Leu Pro Ala Asn Gly Gly Ser Tyr
            20                  25                  30

Gln Arg Trp Thr Gly Pro Gly Asp Gly Thr Val Arg Asn Ala Glu Thr
        35                  40                  45

Gly Arg Leu Leu Asp Ser Asn Tyr Asp Gly Ala Val Tyr Thr Leu Pro
    50                  55                  60

Ala Asn Gly Gly Ser Tyr Gln Lys Trp Thr Gly Pro Gly Asp Gly Thr
65                  70                  75                  80

Ile Gln Asn Ala Glu Thr Gly Arg Leu Leu Asp Ser Asn Tyr Asp Gly
```

```
                85                  90                  95

Ala Val Tyr Thr Leu Pro Ala Asn Gly Gly Ser Tyr Gln Lys Trp Thr
            100                 105                 110

Gly


<210> SEQ ID NO 7
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 7

Ala Ser Gly Thr Ile Arg Asn Ala Gln Thr Gly Arg Leu Leu Asp Ser
1               5                   10                  15

Asn Tyr Asn Gly Asn Val Tyr Thr Leu Pro Ala Asn Gly Gly Asn Tyr
            20                  25                  30

Gln Arg Trp Thr Gly Pro Gly Asp Gly Thr Val Arg Asn Ala Gln Thr
        35                  40                  45

Gly Arg Leu Leu Asp Ser Asn Tyr Asn Gly Asn Val Tyr Thr Leu Pro
    50                  55                  60

Ala Asn Gly Gly Asn Tyr Gln Lys Trp Thr Gly Pro Gly Asp Gly Thr
65                  70                  75                  80

Ile Gln Asn Ala Gln Thr Gly Arg Val Leu Asp Ser Asn Tyr Asn Gly
                85                  90                  95

Asn Val Tyr Thr Leu Pro Ala Asn Gly Gly Asn Tyr Gln Lys Trp Thr
            100                 105                 110

Gly


<210> SEQ ID NO 8
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 8

Ala Ser Gly Thr Ile Arg Asn Ala Glu Thr Gly Arg Leu Leu Asp Ser
1               5                   10                  15

Asn Tyr Asn Gly Asn Val Tyr Thr Leu Pro Ala Asn Gly Gly Asn Tyr
            20                  25                  30

Gln Arg Trp Thr Gly Pro Gly Asp Gly Thr Val Arg Asn Ala Glu Thr
        35                  40                  45

Gly Arg Leu Leu Asp Ser Asn Tyr Asn Gly Asn Val Tyr Thr Leu Pro
    50                  55                  60

Ala Asn Gly Gly Asn Tyr Gln Lys Trp Thr Gly Pro Gly Asp Gly Thr
65                  70                  75                  80

Ile Gln Asn Ala Glu Thr Gly Arg Val Leu Asp Ser Asn Tyr Asn Gly
                85                  90                  95

Asn Val Tyr Thr Leu Pro Ala Asn Gly Gly Asn Tyr Gln Lys Trp Thr
            100                 105                 110

Gly


<210> SEQ ID NO 9
<211> LENGTH: 114
<212> TYPE: PRT
<213> ORGANISM: Artificial Sequence
<220> FEATURE:
```

<223> OTHER INFORMATION: Actinohivin Variant Polypeptide

<400> SEQUENCE: 9

Ala Ser Val Thr Ile Arg Asn Ala Glu Thr Gly Arg Leu Leu Asp Ser
1 5 10 15

Asn Tyr Asn Gly Asn Val Tyr Thr Leu Pro Ala Asn Gly Gly Asn Tyr
20 25 30

Gln Arg Trp Thr Gly Pro Gly Asp Gly Thr Val Arg Asn Ala Glu Thr
35 40 45

Gly Arg Cys Leu Asp Ser Asn Tyr Asp Gly Ala Val Tyr Thr Leu Pro
50 55 60

Cys Asn Gly Gly Ser Tyr Gln Lys Trp Leu Phe Tyr Ser Asn Gly Tyr
65 70 75 80

Ile Gln Asn Val Glu Thr Gly Arg Val Leu Asp Ser Asn Tyr Asn Gly
85 90 95

Asn Val Tyr Thr Leu Pro Ala Asn Gly Gly Asn Tyr Gln Lys Trp Tyr
100 105 110

Thr Gly

<210> SEQ ID NO 10
<211> LENGTH: 114
<212> TYPE: PRT
<213> ORGANISM: Artificial Sequence
<220> FEATURE:
<223> OTHER INFORMATION: Actinohivin Variant Polypeptide

<400> SEQUENCE: 10

Ala Ser Val Thr Ile Arg Asn Ala Glu Thr Gly Arg Cys Leu Asp Ser
1 5 10 15

Asn Tyr Asn Gly Asn Val Tyr Thr Leu Pro Cys Asn Gly Gly Asn Tyr
20 25 30

Gln Arg Trp Thr Gly Pro Gly Asp Gly Thr Val Arg Asn Ala Glu Thr
35 40 45

Gly Arg Cys Leu Asp Ser Asn Tyr Asp Gly Ala Val Tyr Thr Leu Pro
50 55 60

Cys Asn Gly Gly Ser Tyr Gln Lys Trp Leu Phe Tyr Ser Asn Gly Tyr
65 70 75 80

Ile Gln Asn Val Glu Thr Gly Arg Cys Leu Asp Ser Asn Tyr Asn Gly
85 90 95

Asn Val Tyr Thr Leu Pro Cys Asn Gly Gly Asn Tyr Gln Lys Trp Tyr
100 105 110

Thr Gly

<210> SEQ ID NO 11
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 11

Ala Ser Gly Thr Ile Arg Asn Ala Glu Thr Gly Arg Leu Leu Asp Ser
1 5 10 15

Asn Tyr Asn Gly Asn Val Tyr Thr Leu Pro Ala Asn Gly Gly Asn Tyr
20 25 30

Gln Arg Trp Thr Gly Pro Gly Asp Gly Thr Val Arg Asn Ala Glu Thr
35 40 45

Gly Arg Cys Leu Asp Ser Asn Tyr Asp Gly Ala Val Tyr Thr Leu Pro
    50                  55                  60

Cys Asn Gly Gly Ser Tyr Gln Lys Trp Thr Gly Pro Gly Asp Gly Thr
65                  70                  75                  80

Ile Gln Asn Ala Glu Thr Gly Arg Val Leu Asp Ser Asn Tyr Asn Gly
                85                  90                  95

Asn Val Tyr Thr Leu Pro Ala Asn Gly Gly Asn Tyr Gln Lys Trp Thr
            100                 105                 110

Gly

<210> SEQ ID NO 12
<211> LENGTH: 113
<212> TYPE: PRT
<213> ORGANISM: Artificial Sequence
<220> FEATURE:
<223> OTHER INFORMATION: Actinohivin Variant Polypeptide

<400> SEQUENCE: 12

Ala Ser Gly Thr Ile Arg Asn Ala Gln Thr Gly Arg Cys Leu Asp Ser
1               5                   10                  15

Asn Tyr Asn Gly Asn Val Tyr Thr Leu Pro Cys Asn Gly Gly Asn Tyr
            20                  25                  30

Gln Arg Trp Thr Gly Pro Gly Asp Gly Thr Val Arg Asn Ala Gln Thr
        35                  40                  45

Gly Arg Cys Leu Asp Ser Asn Tyr Asp Gly Ala Val Tyr Thr Leu Pro
    50                  55                  60

Cys Asn Gly Gly Ser Tyr Gln Lys Trp Thr Gly Pro Gly Asp Gly Thr
65                  70                  75                  80

Ile Gln Asn Ala Glu Thr Gly Arg Cys Leu Asp Ser Asn Tyr Asn Gly
                85                  90                  95

Asn Val Tyr Thr Leu Pro Cys Asn Gly Gly Asn Tyr Gln Lys Trp Thr
            100                 105                 110

Gly

<210> SEQ ID NO 13
<211> LENGTH: 4
<212> TYPE: PRT
<213> ORGANISM: Artificial Sequence
<220> FEATURE:
<223> OTHER INFORMATION: Peptide Linker

<400> SEQUENCE: 13

Gly Gly Gly Ser
1

<210> SEQ ID NO 14
<211> LENGTH: 78
<212> TYPE: DNA
<213> ORGANISM: Artificial Sequence
<220> FEATURE:
<223> OTHER INFORMATION: Nucleic Acid Sequence for Endomembrane System
      Signal Peptide

<400> SEQUENCE: 14
atggggaagc aaatggccgc cctgtgtggc tttctcctcg tggcgttgct ctggctcacg     60
cccgacgtcg cgcatggt                                                   78

<210> SEQ ID NO 15
<211> LENGTH: 26
<212> TYPE: PRT

-continued

```
<213> ORGANISM: Artificial Sequence
<220> FEATURE:
<223> OTHER INFORMATION: Endomembrane System Signal Peptide

<400> SEQUENCE: 15

Met Gly Lys Gln Met Ala Ala Leu Cys Gly Phe Leu Leu Val Ala Leu
1               5                   10                  15

Leu Trp Leu Thr Pro Asp Val Ala His Gly
            20                  25
```